(12) United States Patent
Chen et al.

(10) Patent No.: US 10,492,822 B2
(45) Date of Patent: Dec. 3, 2019

(54) CONCENTRIC CUTTING DEVICES FOR USE IN MINIMALLY INVASIVE MEDICAL PROCEDURES

(71) Applicant: Microfabrica Inc., Van Nuys, CA (US)

(72) Inventors: Richard T. Chen, Woodland Hills, CA (US); Ming-Ting Wu, Northridge, CA (US); Arun Veeramani, Woodland Hills, CA (US); Vacit Arat, La Canada Flintridge, CA (US); Gregory P. Schmitz, Los Gatos, CA (US)

(73) Assignee: Microfabrica Inc., Van Nuys, CA (US)

( * ) Notice: Subject to any disclaimer, the term of this patent is extended or adjusted under 35 U.S.C. 154(b) by 219 days.

(21) Appl. No.: 14/181,247

(22) Filed: Feb. 14, 2014

(65) Prior Publication Data

US 2014/0163596 A1    Jun. 12, 2014

Related U.S. Application Data

(63) Continuation of application No. 13/388,653, filed as application No. PCT/US2010/045951 on Aug. 18, 2010, now abandoned.
(Continued)

(51) Int. Cl.
*A61B 17/3207* (2006.01)
*A61B 10/02* (2006.01)
(Continued)

(52) U.S. Cl.
CPC .. *A61B 17/320758* (2013.01); *A61B 10/0266* (2013.01); *A61B 17/32002* (2013.01);
(Continued)

(58) Field of Classification Search
CPC .......... A61B 10/0266; A61B 17/32002; A61B 17/320758; A61B 2017/00345; A61B 2017/320775
(Continued)

(56) References Cited

U.S. PATENT DOCUMENTS 1,179,910 A    4/1916  Greenfield
1,817,000 A    8/1931  Bernard
(Continued)

FOREIGN PATENT DOCUMENTS

DE    202008013915 U    3/2009
EP    0572131 A1    12/1993
(Continued)

OTHER PUBLICATIONS

Cohen et al.; EFAB: Batch production of functional, fully-dense metal parts with micron-scale features; Proc 9th, Solid Freeform Fabrication; Univ. of Texas at Austin; pp. 161-168; Aug. 1998.
(Continued)

*Primary Examiner* — Sarah A Simpson
(74) *Attorney, Agent, or Firm* — Dennis R. Smalley

(57) ABSTRACT

Various embodiments of a tissue cutting device are described, such as a device with an elongate tube having a proximal end and a distal end and a central axis extending from the proximal end to the distal end; a first annular element at the distal end of the elongate tube, the first annular element having a flat portion at its distal end perpendicular to the central axis; and a second annular element at the distal end of the elongate tube and concentric with the first annular element, the second annular element having a flat portion at its distal end perpendicular to the central axis, at least one of the first or second annular elements rotatable about the central axis, the rotation causing the first annular element and the second annular element to pass each other to shear tissue.

21 Claims, 28 Drawing Sheets

Related U.S. Application Data

(60) Provisional application No. 61/234,989, filed on Aug. 18, 2009.

(51) Int. Cl.
    *A61B 17/32* (2006.01)
    *A61B 17/3203* (2006.01)
    *A61B 17/3205* (2006.01)
    *A61B 17/00* (2006.01)

(52) U.S. Cl.
    CPC ...... *A61B 17/3203* (2013.01); *A61B 17/3205* (2013.01); *A61B 10/0283* (2013.01); *A61B 2017/00345* (2013.01); *A61B 2017/00526* (2013.01); *A61B 2017/320064* (2013.01); *A61B 2017/320775* (2013.01)

(58) Field of Classification Search
    USPC ....................................................... 606/180
    See application file for complete search history.

(56) References Cited

U.S. PATENT DOCUMENTS

| | | |
|---|---|---|
| 2,259,015 A | 10/1941 | Anderson et al. |
| 2,455,655 A | 12/1948 | Carroll |
| 3,404,677 A | 10/1968 | Springer |
| 3,882,872 A | 5/1975 | Douvas et al. |
| 3,937,222 A | 2/1976 | Banko |
| 4,197,645 A | 4/1980 | Schiecher |
| 4,334,650 A | 6/1982 | Hardwick et al. |
| 4,598,710 A | 7/1986 | Kleinberg et al. |
| 4,621,637 A | 11/1986 | Fishbein |
| 4,747,821 A | 5/1988 | Kensey et al. |
| 4,804,364 A | 2/1989 | Dieras et al. |
| 4,842,578 A | 6/1989 | Johnson et al. |
| 4,844,363 A | 7/1989 | Garnier et al. |
| 4,854,808 A | 8/1989 | Bisiach |
| 4,943,296 A | 7/1990 | Funakubo et al. |
| 4,983,179 A | 1/1991 | Sjostrom |
| 4,986,807 A | 1/1991 | Farr |
| 5,019,088 A | 5/1991 | Farr |
| 5,084,052 A | 1/1992 | Jacobs |
| 5,141,168 A | 8/1992 | Pepper |
| 5,160,095 A | 11/1992 | Pepper |
| 5,181,433 A | 1/1993 | Ueno et al. |
| 5,190,637 A | 3/1993 | Guckel |
| 5,226,909 A | 7/1993 | Evans et al. |
| 5,284,486 A | 2/1994 | Kotula et al. |
| 5,378,583 A | 1/1995 | Guckel et al. |
| 5,411,511 A | 5/1995 | Hall |
| 5,465,444 A | 11/1995 | Bigler et al. |
| 5,484,112 A | 1/1996 | Koenig |
| 5,496,668 A | 3/1996 | Guckel et al. |
| 5,522,829 A | 6/1996 | Michalos |
| 5,549,637 A | 8/1996 | Crainich |
| 5,575,799 A | 11/1996 | Bolanos et al. |
| 5,576,147 A | 11/1996 | Guckel et al. |
| 5,591,187 A | 1/1997 | Dekel |
| 5,601,556 A | 2/1997 | Pisharodi |
| 5,618,293 A | 4/1997 | Sample et al. |
| 5,643,304 A | 7/1997 | Schechter et al. |
| 5,662,284 A | 9/1997 | Koenig |
| 5,676,321 A * | 10/1997 | Kroger ............ 241/236 |
| 5,685,838 A | 11/1997 | Peters et al. |
| 5,693,063 A | 12/1997 | Van Wyk et al. |
| 5,695,510 A | 12/1997 | Hood |
| 5,718,618 A | 2/1998 | Guckel et al. |
| 5,725,530 A | 3/1998 | Popken |
| 5,779,713 A | 7/1998 | Turjanski et al. |
| 5,782,848 A | 7/1998 | Lennox |
| 5,788,169 A | 8/1998 | Koenig |
| 5,810,809 A | 9/1998 | Rydell |
| 5,823,990 A | 10/1998 | Henley |
| 5,846,244 A | 12/1998 | Cripe |
| 5,863,294 A | 1/1999 | Alden |
| 5,866,281 A | 2/1999 | Guckel et al. |
| 5,908,719 A | 6/1999 | Guckel et al. |
| 5,910,150 A | 6/1999 | Saadat |
| 5,916,231 A | 6/1999 | Bays |
| 5,928,158 A | 7/1999 | Aristides |
| 5,928,161 A | 7/1999 | Krulevitch et al. |
| 5,957,881 A | 9/1999 | Peters et al. |
| 6,001,112 A | 12/1999 | Taylor |
| 6,010,477 A | 1/2000 | Bays |
| 6,013,991 A | 1/2000 | Philipp |
| 6,027,630 A | 2/2000 | Cohen |
| 6,063,088 A | 5/2000 | Winslow |
| 6,129,698 A | 10/2000 | Beck |
| 6,190,385 B1 | 2/2001 | Tom et al. |
| 6,217,598 B1 | 4/2001 | Berman |
| 6,221,088 B1 | 4/2001 | Bays |
| 6,238,405 B1 | 5/2001 | Findlay et al. |
| 6,293,957 B1 | 9/2001 | Peters et al. |
| 6,402,070 B1 | 6/2002 | Ishida et al. |
| 6,447,525 B2 | 9/2002 | Follmer et al. |
| 6,454,717 B1 | 9/2002 | Pantages et al. |
| 6,475,369 B1 | 11/2002 | Cohen |
| 6,503,263 B2 | 1/2003 | Adams |
| 6,517,544 B1 | 2/2003 | Michelson |
| 6,565,588 B1 | 5/2003 | Clement et al. |
| 6,572,613 B1 | 6/2003 | Ellman et al. |
| 6,572,742 B1 | 6/2003 | Cohen |
| 6,613,972 B2 | 9/2003 | Cohen et al. |
| 6,663,031 B2 | 12/2003 | Henderson et al. |
| 6,666,874 B2 | 12/2003 | Heitzmann et al. |
| 6,753,952 B1 | 6/2004 | Lawrence et al. |
| 6,761,723 B2 | 7/2004 | Buttermann et al. |
| 6,790,377 B1 | 9/2004 | Cohen |
| 6,951,456 B2 | 10/2005 | Cohen et al. |
| 6,994,708 B2 | 2/2006 | Manzo |
| 7,052,494 B2 | 5/2006 | Goble et al. |
| 7,160,304 B2 | 1/2007 | Michelson |
| 7,163,614 B2 | 1/2007 | Cohen |
| 7,195,989 B2 | 3/2007 | Lockard et al. |
| 7,229,544 B2 | 6/2007 | Cohen |
| 7,235,088 B2 | 6/2007 | Pintor et al. |
| 7,239,219 B2 | 7/2007 | Brown et al. |
| 7,252,861 B2 | 8/2007 | Smalley |
| 7,479,147 B2 | 1/2009 | Honeycutt et al. |
| 7,540,867 B2 | 6/2009 | Jinno et al. |
| 7,553,307 B2 | 6/2009 | Bleich et al. |
| 7,699,790 B2 | 4/2010 | Simpson |
| 7,918,849 B2 | 4/2011 | Bleich et al. |
| 8,002,776 B2 | 8/2011 | Liu et al. |
| 8,034,003 B2 | 10/2011 | Pesce et al. |
| 8,114,074 B1 | 2/2012 | Slater |
| 8,146,400 B2 | 4/2012 | Goldfarb et al. |
| 8,292,889 B2 | 10/2012 | Cunningham et al. |
| 8,326,414 B2 | 12/2012 | Neubardt et al. |
| 8,409,235 B2 | 4/2013 | Rubin |
| 8,414,607 B1 | 4/2013 | Lockard et al. |
| 8,475,458 B2 | 7/2013 | Lockard et al. |
| 8,475,483 B2 | 7/2013 | Schmitz et al. |
| 8,486,096 B2 | 7/2013 | Robertson et al. |
| 8,512,342 B2 | 8/2013 | Meredith |
| 8,715,281 B2 | 5/2014 | Barlow et al. |
| 2001/0000531 A1 | 4/2001 | Casscells et al. |
| 2001/0041307 A1 | 11/2001 | Lee et al. |
| 2002/0058944 A1 | 5/2002 | Michelson |
| 2002/0099367 A1 | 7/2002 | Guo et al. |
| 2002/0123763 A1 | 9/2002 | Blake |
| 2002/0138088 A1 | 9/2002 | Nash et al. |
| 2003/0144681 A1 | 7/2003 | Sample |
| 2003/0163126 A1 | 8/2003 | West |
| 2003/0179364 A1 | 9/2003 | Steenblik et al. |
| 2004/0138672 A1 | 7/2004 | Michelson |
| 2005/0021065 A1 | 1/2005 | Yamada et al. |
| 2005/0029109 A1 | 2/2005 | Zhang et al. |
| 2005/0054972 A1 | 3/2005 | Adams et al. |
| 2005/0059905 A1 | 3/2005 | Boock et al. |
| 2005/0090848 A1 | 4/2005 | Adams |
| 2005/0222598 A1 | 10/2005 | Ho et al. |
| 2006/0089662 A1 | 4/2006 | Davison et al. |

(56) References Cited

U.S. PATENT DOCUMENTS

| | | |
|---|---|---|
| 2006/0161185 A1 | 7/2006 | Saadat et al. |
| 2006/0184175 A1 | 8/2006 | Schomer et al. |
| 2006/0200152 A1 | 9/2006 | Karubian et al. |
| 2006/0212060 A1 | 9/2006 | Hacker et al. |
| 2006/0217730 A1 | 9/2006 | Termanini |
| 2006/0224160 A1 | 10/2006 | Trieu et al. |
| 2006/0229624 A1 | 10/2006 | May et al. |
| 2006/0229646 A1 | 10/2006 | Sparks |
| 2006/0241566 A1 | 10/2006 | Moon et al. |
| 2006/0276782 A1 | 12/2006 | Gedebou |
| 2006/0282065 A1 | 12/2006 | Cohen |
| 2007/0016225 A1 | 1/2007 | Nakao |
| 2007/0073303 A1 | 3/2007 | Namba |
| 2007/0100361 A1 | 5/2007 | Cohen |
| 2007/0162062 A1 | 7/2007 | Norton et al. |
| 2007/0173872 A1 | 7/2007 | Neuenfeldt |
| 2007/0197895 A1 | 8/2007 | Nycz et al. |
| 2007/0198038 A1 | 8/2007 | Cohen et al. |
| 2007/0219459 A1 | 9/2007 | Cohen |
| 2007/0260253 A1 | 11/2007 | Johnson et al. |
| 2007/0265648 A1 | 11/2007 | Cohen |
| 2008/0004643 A1 | 1/2008 | To et al. |
| 2008/0009697 A1 | 1/2008 | Haider et al. |
| 2008/0027427 A1 | 1/2008 | Falkenstein et al. |
| 2008/0065125 A1 | 3/2008 | Olson |
| 2008/0091074 A1 | 4/2008 | Kumar et al. |
| 2008/0091224 A1* | 4/2008 | Griffis et al. ............ 606/166 |
| 2008/0103504 A1 | 5/2008 | Schmitz et al. |
| 2008/0161809 A1 | 7/2008 | Schmitz et al. |
| 2008/0249553 A1 | 10/2008 | Gruber et al. |
| 2009/0012524 A1 | 1/2009 | Dower |
| 2009/0018565 A1* | 1/2009 | To et al. ............... 606/159 |
| 2009/0018566 A1 | 1/2009 | Escudero et al. |
| 2009/0124975 A1 | 5/2009 | Oliver et al. |
| 2009/0228030 A1 | 9/2009 | Shadeck |
| 2009/0234378 A1 | 9/2009 | Escudero et al. |
| 2009/0270812 A1 | 10/2009 | Litscher et al. |
| 2009/0306773 A1* | 12/2009 | Silversrini et al. .......... 623/5.11 |
| 2010/0010525 A1 | 1/2010 | Lockard et al. |
| 2010/0030216 A1 | 2/2010 | Arcenio |
| 2010/0094320 A1 | 4/2010 | Arat et al. |
| 2010/0152758 A1 | 6/2010 | Mark et al. |
| 2010/0160916 A1 | 6/2010 | Chana et al. |
| 2010/0191266 A1 | 7/2010 | Oliver et al. |
| 2010/0204560 A1 | 8/2010 | Salahieh et al. |
| 2010/0217268 A1 | 8/2010 | Bloebaum et al. |
| 2010/0305595 A1 | 12/2010 | Hermann |
| 2011/0112563 A1 | 5/2011 | To et al. |
| 2011/0190738 A1 | 8/2011 | Zemlok et al. |
| 2011/0230727 A1 | 9/2011 | Sanders et al. |
| 2011/0288573 A1 | 11/2011 | Yates et al. |
| 2012/0041263 A1 | 2/2012 | Sholev |
| 2012/0109024 A1 | 5/2012 | Theuer |
| 2012/0109172 A1 | 5/2012 | Schmitz et al. |
| 2012/0191121 A1 | 7/2012 | Chen et al. |
| 2012/0221035 A1 | 8/2012 | Harvey |
| 2013/0012975 A1 | 1/2013 | Schmitz et al. |
| 2013/0226209 A1 | 8/2013 | Lockard et al. |
| 2014/0350567 A1 | 11/2014 | Schmitz et al. |
| 2015/0173788 A1 | 6/2015 | Lockard et al. |
| 2015/0265336 A1 | 9/2015 | Schmitz et al. |
| 2016/0135831 A1 | 5/2016 | Schmitz et al. |

FOREIGN PATENT DOCUMENTS

| | | |
|---|---|---|
| EP | 0925857 A2 | 6/1999 |
| EP | 1256319 A2 | 11/2002 |
| EP | 1026996 B1 | 10/2007 |
| WO | WO93/05719 A1 | 4/1993 |
| WO | WO99/63891 A1 | 12/1999 |
| WO | WO02/49518 A2 | 6/2002 |
| WO | WO02/062226 A1 | 8/2002 |
| WO | WO2004/069498 A2 | 8/2004 |
| WO | WO 2008/037984 A2 | 4/2008 |

OTHER PUBLICATIONS

Cohen et al.; EFAB: low-cost automated electrochemical batch fabrication of abritrary 3-D microstructures; Micromachining and Microfabrication Process Technology, SPIE 1999 Symposium on Micromachining and Microfabrication; 11 pgs.; Sep. 1999.

Cohen et al.; EFAB: Rapid, low-cost desktop micromachining of high aspect ratio true 3-D MEMS; Proc. 12th, IEEE Micro Electro Mechanical Systems Workshop; IEEE; pp. 244-251; Jan. 1999.

Cohen, Adam L.; 3-D micromachining by electrochemical fabrication; Micromachine Devices; pp. 6-7; Mar. 1999.

Cohen, Adam L.; Electrochemical Fabrication (EFAB}); MEMS Handbook; Chapter 19; CRC Press LLC; pp. 19-1-19-23; Jan. 7, 2002.

Microfabrication—rapid prototyping's killer application; Rapid Prototyping Report; vol. 9; No. 6; pp. 1-5; Jun. 1999.

SSI Shredding Systems; www.ssiworld.com; 16 pgs.; Sep. 24, 2009 (downloaded).

Tseng et al.; EFAB: high aspect ratio, arbitrary 3-D metal microstructures using a low-cost automated batch process; 3rd Int'l. Workshop on High Aspect Ratio Microstructure Technology (HARMST99); Kazusa, Japan; 4 pgs.; Jun. 1999.

Tseng et al.; EFAB: high aspect ratio, arbitrary 3-D metal microstructures using a low-cost automated batch process; Microelectromechanical Systems (MEMS); vol. 1; ASME 1999 (Int'l. Mechanical Engineering Congress and Exposition; 6 pgs.; Nov. 1999.

Zhang et al.; EFAB: rapid desktop manufacturing of true 3-D microstructures; Proc. 2nd Int'l. Conf. on Integrated MicroNanotechnology for Space Applications; The Aerospace Co.; 11 pgs.; Apr. 1999.

Schmitz et al.; U.S. Appl. No. 13/659,734 entitled "Minimally Invasive Micro Tissue Debriders Having Targeted Rotor Positions," filed Oct. 24, 2012.

Schmitz et al.; U.S. Appl. No. 13/714,285 entitled "Micro Debrider Devices and Methods of Tissue Removal," filed Dec. 13, 2012.

Schmitz et al.; U.S. Appl. No. 13/843,462 entitled "MEMS Debrider Drive Train," filed Mar. 15, 2013.

Schmitz et al.; U.S. Appl. No. 13/855,627 entitled "Micro-articulated surgical instruments using micro gear actuation," filed Apr. 2, 2013.

Schmitz et al.; U.S. Appl. No. 14/033,397 entitled "Micro-Mechanical Devices and Methods for Brain Tumor Removal," filed Sep. 20, 2013.

Schmitz et al.; U.S. Appl. No. 14/333,458 entitled "Counterfeiting deterent and security devices, systems, and methods," filed Jul. 16, 2014.

Bovie Medical Corporation; Resistick II(TM) Coated Electrodes (product information); 2 pgs.; retrieved from the internet (http://www.boviemedical.com/products_aaronresistickelect.asp); print/retrieval date: Apr. 6, 2016.

Jho et al.; Endoscopy assisted transsphenoidal surgery for pituitary adenoma; Acta Neurochirurgica; 138 (12); pp. 1416-1425; 1996 (year of pub. sufficiently earlier than effective US filing date and any foreign priority date).

* cited by examiner

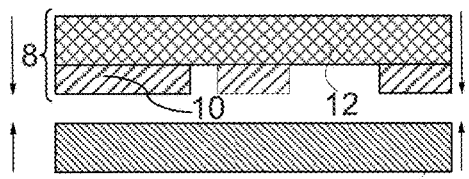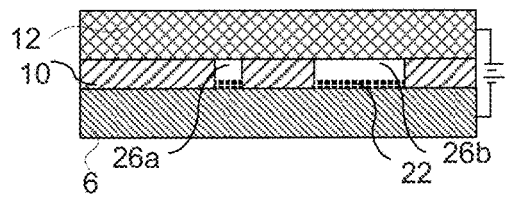

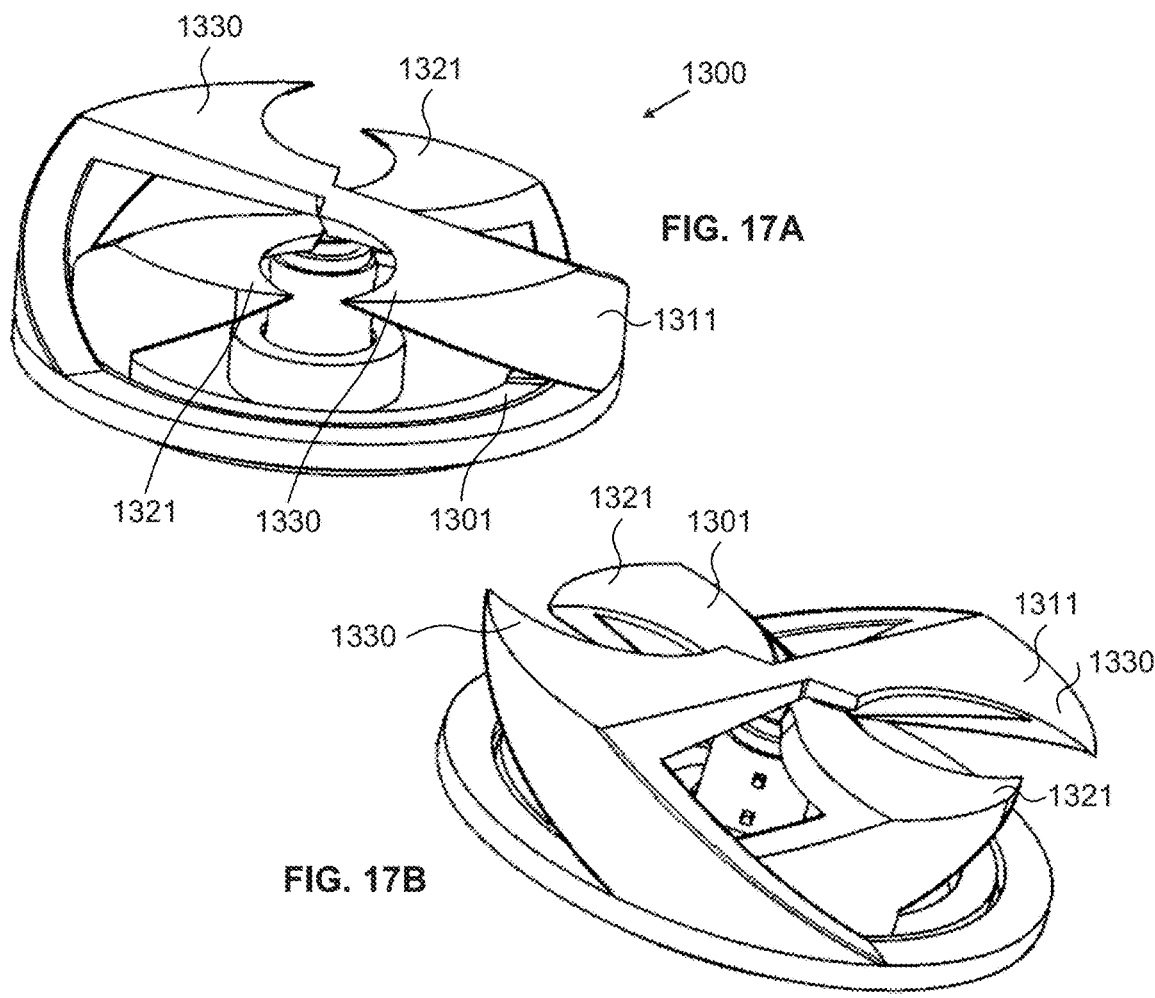
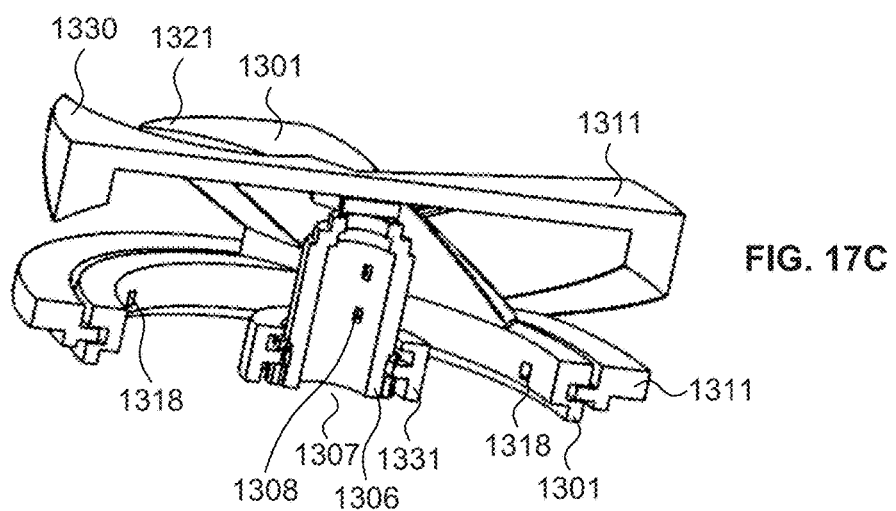

CONCENTRIC CUTTING DEVICES FOR USE IN MINIMALLY INVASIVE MEDICAL PROCEDURES

CROSS-REFERENCE TO RELATED APPLICATIONS

This Application is a continuation of U.S. application Ser. No. 13/388,653, filed Apr. 16, 2012, entitled "Concentric Cutting Devices for Use in Minimally Invasive Medical Procedures," which is a 371 of PCT/US2010/045951, filed Aug. 18, 2010, entitled "Concentric Cutting Devices for Use in Minimally Invasive Medical Procedures," which claims benefit of U.S. Application No. 61/234,989, filed Aug. 18, 2009, entitled "Concentric Cutting Devices for Use in Minimally Invasive Medical Procedures," which are incorporated by reference as if fully set forth herein.

STATEMENT AS TO FEDERALLY SPONSORED RESEARCH

This invention was made with government support under Grant No. R01 HL087797 awarded by the National Institutes of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the present invention relate to micro-scale and millimeter-scale cutting devices that may be located at the distal ends of, or at intermediate positions along the length of, a lumen to provide material cutting, shredding, and removal. Such devices may, for example, be used to remove unwanted tissue or other material from selected locations within a body of a patient during minimally invasive or other medical procedures. In some embodiments, such devices may be used for non-medical procedure and in some embodiments the devices may be made in whole or in part using multi-layer, multi-material fabrication methods such as electrochemical fabrication methods.

BACKGROUND

Electrochemical Fabrication:

An electrochemical fabrication technique for forming three-dimensional structures from a plurality of adhered layers is being commercially pursued by Microfabrica® Inc. (formerly MEMGen Corporation) of Van Nuys, Calif. under the name EFAB®.

Various electrochemical fabrication techniques were described in U.S. Pat. No. 6,027,630, issued on Feb. 22, 2000 to Adam Cohen. Some embodiments of this electrochemical fabrication technique allows the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate, while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. such masks have come to be known as INSTANT MASKS™ and the process known as INSTANT MASKING or INSTANT MASK™ plating. Selective depositions using conformable contact mask plating may be used to form single selective deposits of material or may be used in a process to form multi-layer structures. The teachings of the '630 patent are hereby incorporated herein by reference as if set forth in full herein. Since the filing of the patent application that led to the above noted patent, various papers about conformable contact mask plating (i.e. INSTANT MASKING) and electrochemical fabrication have been published:

(1) A. Cohen, G. Zhang, F. Tseng, F. Mansfeld, U. Frodis and P. Will, "EFAB: Batch production of functional, fully-dense metal parts with micro-scale features", Proc. 9th Solid Freeform Fabrication, The University of Texas at Austin, p161, August 1998.

(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p244, January 1999.

(3) A. Cohen, "3-D Micromachining by Electrochemical Fabrication", Micromachine Devices, March 1999.

(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.

(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.

(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.

(7) F. Tseng, G. Zhang, U. Frodis, A. Cohen, F. Mansfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.

(8) A. Cohen, "Electrochemical Fabrication (EFAB™)", Chapter 19 of The MEMS Handbook, edited by Mohamed Gad-El-Hak, CRC Press, 2002.

(9) Microfabrication—Rapid Prototyping's Killer Application", pages 1-5 of the Rapid Prototyping Report, CAD/CAM Publishing, Inc., June 1999.

The disclosures of these nine publications are hereby incorporated herein by reference as if set forth in full herein.

An electrochemical deposition for forming multilayer structures may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate. Typically this material is either a structural material or a sacrificial material.

2. Then, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.

3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to an immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated (the pattern of conformable material is complementary to the pattern of material to be deposited). At least one CC mask is used for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for multiple CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of (1) the substrate, (2) a previously formed layer, or (3) a previously deposited portion of a layer on which deposition is to occur. The pressing together of the CC mask and relevant substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6, separated from mask 8, onto which material will be deposited during the process of forming a layer. CC mask plating selectively deposits material 22 onto substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C.

The CC mask plating process is distinct from a "through-mask" plating process in that in a through-mask plating process the separation of the masking material from the substrate would occur destructively. Furthermore in a through mask plating process, opening in the masking material are typically formed while the masking material is in contact with and adhered to the substrate. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the substrate on which plating is to occur (e.g. separate from a three-dimensional (3D) structure that is being formed). CC masks may be formed in a variety of ways, for example, using a photolithographic process. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask 8, the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode/substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C. The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 12, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated. In such embodiments, the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing through mask exposures. A first layer of a primary metal is electroplated onto an exposed plating base to fill a void in a photoresist (the photoresist forming a through mask having a desired pattern of openings), the photoresist is then removed and a secondary metal is electroplated over the first layer and over the plating base. The exposed surface of the secondary metal is then machined down to a height which exposes the first metal to produce a flat uniform surface extending across both the primary and secondary metals. Formation of a second layer may then begin by applying a photoresist over the first layer and patterning it (i.e. to form a second through mask) and then repeating the process that was used to produce the first layer to produce a second layer of desired configuration. The process is repeated until the entire structure is formed and the secondary metal is removed by etching. The photoresist is formed over the plating base or previous layer by casting and patterning of the photoresist (i.e. voids formed in the photoresist) are formed by exposure of the photoresist through a patterned mask via X-rays or UV radiation and development of the exposed or unexposed areas.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial layer of sacrificial material (i.e. a layer or coating of a single material) on the substrate so that the structure and substrate may be detached if desired. In such cases after formation of the structure the sacrificial material forming part of each layer of the structure may be removed along the initial sacrificial layer to free the structure. Substrate materials mentioned in the '637 patent include silicon, glass, metals, and silicon with protected semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within various fields to produce new structures, certain uses for Electrochemical Fabrication provide designs, structures, capabilities and/or features not known or obvious in view of the state of the art.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

Material Removal Devices for Medical Applications

Various mechanical material breakdown and/or removal methods and devices have been proposed and/or used in minimally invasive medical applications such as thrombectomy and atherectomy procedures. These devices can be used in medical procedures including planning, coring, milling, and drilling. Such devices, for example, have included the use of cutting elements, shaving elements, and grinding elements. Examples of cutting devices are found, for example in (1) US Patent Application Publication No. 2006/0212060 A1, entitled "Arthroscopic Shaver and Method of Manufacturing Same" by Randall L. Hacker, et al. and assigned to Arthex, Inc.; (2) U.S. Pat. No. 6,447,525; (3) U.S. Pat. No. 7,479,147; and (4) U.S. Pat. No. 7,235,088.

Planing devices can be used to surface thin layers of tissue, e.g. for removing scars from the surface of the skin. Conventional planing devices include at least one sharp edge that can be translated across the tissue to remove the top-most layer. Such cutting surfaces in conventional planing devices generally have dimensions that are too large to cut thin slices of tissue, e.g. to cut slices of tissue having a thickness less than 50 μm, and these devices therefore cannot precisely remove small areas of tissue.

Coring devices can be used for biopsying tissue. Conventional coring devices generally include a needle that bores into the tissue. Conventional coring devices tend to cause pulling of and damage to surrounding tissue as the needle is pushed in. The rapid forward movement of the needle can also push aside the target tissue, such as a suspected tumor, especially if the target tissue is firmer than the surrounding tissue. Further, conventional coring devices do not have small enough feature sizes to remove only small tissue particles, again resulting in excessive damage to surrounding tissue.

Milling devices, such as debriders, can be used for de-bulking, e.g. for surgical removal of a malignant tumor. Conventional debriders include a rounded or pointed distal end to aid in removing specific tissue. However, such conventional milling devices are disadvantageous in that they often remove too much tissue and, due to their rounded ends, cannot selectively remove surface tissue. Further, conventional milling devices have dimensions that are generally too large to precisely remove small areas of tissue.

Drilling devices, such as atherectomy devices, are used to cut through tissue in the body. For example, atherectomy devices are used to treat atherosclerosis, in which the arteries are obstructed due to the accumulation of plaque and neointimal hyperplasia. Such atherectomy devices work by cutting away or excising the obstructing plaque to help restore blood flow. Drilling devices are configured in a variety of ways, but generally include employing a rotatable and/or axially translatable cutting blade or abrasive end which can be advanced into the occluding material and rotated or translated to cut away the desired material. Conventional drilling devices, however, have several drawbacks. Namely, the minimum feature size and shape of such devices, e.g. the size and shape of the cutting blades, are often too large to cut specifically and precisely, such as down to a micrometer or cellular scale. As a result, such devices tend to either leave unwanted tissue in the body, such as plaque in the blood vessel, or cut too much tissue, thereby injuring surrounding tissue. Further, traditional drilling devices have a fairly large diameter, e.g. over 2 mm, and are not configured to fit into small lumens, such as blood vessels, having a smaller diameter. As a result, some areas in the body are unreachable by conventional drilling devices.

Accordingly, there is a need for small tissue-cutting devices, such as planing, coring, milling, or drilling devices, that can precisely cut tissue down to a micrometer or cellular scale.

SUMMARY OF THE DISCLOSURE

It is an object of some embodiments of the invention to provide an improved method for forming multi-layer three-dimensional structures It is an object of some embodiments of the invention to provide improved millimeter-scale or micro-scale devices that may be used in minimally invasive procedure to provide therapeutic, diagnostic, or preventive treatment.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

One aspect of the invention provides a tissue cutting device with an elongate tube having a proximal end and a distal end and a central axis extending from the proximal end to the distal end; a first annular element at the distal end of the elongate tube, the first annular element having a flat portion at its distal end perpendicular to the central axis, the flat portion extending from an outer circumference of the first annular element to the central axis; and a second annular element at the distal end of the elongate tube and concentric with the first annular element, the second annular element having a flat portion at its distal end perpendicular to the central axis, at least one of the first or second annular elements rotatable about the central axis, the rotation causing the first annular element and the second annular element to pass each other to shear tissue. In various embodiments, the elongate tube may have a diameter less than 5 mm, at least one of the first and second annular elements may have a tooth having a radial thickness of less than 50 microns, and/or the flat portion may have an axial thickness of less than 100 microns. Some embodiments of the invention have an intake window at the distal end of the elongate tube.

In some embodiments, the first annular element is rotatable about the central axis in an opposite direction from the second annular element. In some embodiments, the first annular element is rotatable about the central axis in a same direction as the second annular element, and the first annular element and the second annular element being configured to be rotated at different speeds.

In some embodiments, the tissue cutting device includes a hole extending along the central axis. In such embodiments, there may also be an ancillary component extending through the hole, such as an imaging element, a guide wire, a water jet tube, or a barbed device.

Some embodiments also have a third annular element and a fourth annular element, the third and fourth annular elements located between the proximal and distal ends, at least one of the third or fourth annular elements configured to rotate, the rotation causing the third and fourth annular elements to rotate past each other to further shear the tissue.

Another aspect of the invention provides a tissue cutting device with an elongate tube having a proximal end and a distal end and a central axis extending from the proximal end to the distal end; a first annular element at the distal end of the elongate tube; a second annular element at the distal end of the elongate tube and concentric with the first annular element, at least one of the first or second annular elements rotatable about the central axis, the rotation causing the first annular element and the second annular element to pass each other to shear tissue; wherein the first and second elements together form a conical shape at the distal end of the elongate tube; and wherein edges of the first and second tubular element are beveled to further shear tissue. In various embodiments the elongate tube may have a diameter less than 5 mm and the beveled edges may have a thickness less than 10 microns.

In some embodiments, the first annular element is rotatable about the central axis in an opposite direction from the second annular element. In some embodiments, the first and second elements together form a second conical shape, the second conical shape facing proximally. In some embodiments the first annular element is rotatable about the central axis in a same direction as the second annular element, the first annular element and the second annular element being configured to be rotated at different speeds.

Some embodiments of the tissue cutting device may have an intake window at the distal end of the elongate tube. Some embodiments may have a hole extending along the central axis and, optionally, an ancillary component extending through the hole, such as an imaging element, a guide wire, a water jet tube, or a barbed device.

In some embodiments, the tissue cutting device includes a third annular element and a fourth annular element, the third and fourth annular elements located between the proximal and distal ends, at least one of the third or fourth annular elements configured to rotate, the rotation causing the third and fourth annular elements to rotate past each other to further shear the tissue.

Yet another aspect of the invention provides a tissue cutting device with an elongate tube having a proximal end and a distal end and a central axis extending from the proximal end to the distal end; a first annular element at the distal end of the elongate tube; a second annular element at the distal end of the elongate tube and concentric with the first annular element, at least one of the first or second annular elements rotatable about the central axis; wherein the first and second annular elements each have an axially-extending cutting surface, the rotation causing the axially-extending surfaces of the first and second annular elements to pass each other to shear tissue, and wherein the first and second annular elements each have a radially-extending cutting surface, rotation causing the axially-extending surfaces of the first and second elements to pass each other to shear tissue, wherein the axially extending cutting surface has an axial length of less than 100 microns.

In some embodiments, the tissue cutting device may have teeth extending along the axially-extending or radially-extending cutting surfaces. In various embodiments the elongate tube may have a diameter less than 0.5 mm.

In some embodiments, the first annular element is rotatable about the central axis in an opposite direction from the second annular element. In some embodiments, the first annular element is rotatable about the central axis in a same direction as the second annular element, the first annular element and the second annular element being configured to be rotated at different speeds.

Some embodiments of the tissue cutting device have an intake window at the distal end of the elongate tube. Some embodiments of the invention have a hole extending along the central axis and, optionally, an ancillary component extending through the hole, such as an imaging element, a guide wire, a water jet tube, or a barbed device.

In some embodiments, the tissue cutting device includes a third annular element and a fourth annular element, the third and fourth annular elements located between the proximal and distal ends, at least one of the third or fourth annular elements configured to rotate, the rotation causing the third and fourth annular elements to rotate past each other to further shear the tissue.

Still another aspect of the invention provides a tissue cutting device with an elongate tube having a proximal end and a distal end and a central axis extending from the proximal end to the distal end; a first annular element at the distal end of the elongate tube; a second annular element at the distal end of the elongate tube and concentric with the first annular element, at least one of the first or second annular elements rotatable about the central axis; wherein the first and second annular elements each include axially-extending teeth, the teeth having a radial thickness of less than 10 microns, the rotation causing the teeth of the first annular element and the teeth of the second annular element to pass each other to shear tissue. In some embodiments, the elongate tube has a diameter less than 5 mm.

In some embodiments, the first annular element is rotatable about the central axis in an opposite direction from the second annular element. In some embodiments, the first annular element is rotatable about the central axis in a same direction as the second annular element, the first annular element and the second annular element being configured to be rotated at different speeds.

In some embodiments of the tissue cutting device, the teeth have a pitch of less than 200 microns. Some embodiments also provide an intake window at the distal end of the elongate tube. In some embodiments, the tissue cutting device includes a hole extending along the central axis and, optionally, an ancillary component extending through the hole, such as an imaging element, a guide wire, a water jet tube, or a barbed device. In some embodiments, the tissue cutting device includes a third annular element and a fourth annular element, the third and fourth annular elements located between the proximal and distal ends, at least one of the third or fourth annular elements configured to rotate, the rotation causing the third and fourth annular elements to rotate past each other to further shear the tissue.

Another aspect of the invention provides a tissue cutting device with an elongate tube having a proximal end and a distal end and a central axis extending from the proximal end to the distal end; a first annular element at the distal end of the elongate tube, the first annular element including a plurality of first shearing elements, each first shearing element having a perpendicular shearing surface that is perpendicular to the central axis; a second annular element at the distal end of the elongate tube and concentric with the first annular element, the second annular element including a plurality of second shearing elements, each second shearing element having a perpendicular shearing surface that is perpendicular to the central axis, wherein at least one of the first or second annular elements is rotatable about the central axis, the rotation causing the perpendicular shearing surfaces of the first shearing elements and the perpendicular shearing surfaces of the second shearing elements to pass each other to shear tissue. In some embodiments, the elongate tube may have a diameter of less than 5 mm.

In some embodiments, at least some of the perpendicular shearing surfaces of the first shearing elements lie along the same plane and, optionally, at least some of the perpendicular shearing surfaces are located at the same radial distance from the central axis.

In some embodiments, at least some of the perpendicular shearing surfaces do not lie along the same plane and, optionally, at least some perpendicular shearing surfaces are located at different radial distances from the central axis.

In some embodiments, each first shearing element has a parallel shearing surface that is parallel to the central axis; wherein each second shearing element has a parallel shearing surface that is parallel to the central axis; and wherein rotation of the second annular element causes the causes the parallel shearing surfaces of the first shearing elements and the parallel shearing surfaces of the second shearing elements to pass each other to shear tissue. In some such embodiments, at least some of the parallel shearing surfaces of the first shearing elements lie along the same radial plane and, optionally, the at least some parallel shearing surfaces are spaced apart from each other circumferentially. In some embodiments, at least some of the parallel shearing surfaces of the first shearing elements are spaced apart from each other radially.

Still another aspect of the invention provides a tissue cutting device with an elongate tube having a proximal end and a distal end and a central axis extending from the proximal end to the distal end; a first annular element at the distal end of the elongate tube, the first annular element including a plurality of first shearing elements, each first shearing element having a parallel shearing surface that is parallel to the central axis; a second annular element at the distal end of the elongate tube and concentric with the first annular element, the second annular element including a plurality of second shearing element, each second shearing element having a parallel shearing surface that is parallel to the central axis, wherein at least one of the first or second annular elements is rotatable about the central axis, the rotation causing the parallel shearing surfaces of the first shearing elements and the parallel shearing surfaces of the second shearing elements to pass each other to shear tissue.

In some embodiments, at least some of the parallel shearing surfaces of the first shearing elements lie along the same radial plane. In some such embodiments, the at least some of the parallel shearing surfaces are spaced apart from each other axially and, optionally, the at least some of the parallel shearing surfaces are spaced apart from each other circumferentially.

In some embodiments, at least some of the parallel shearing surfaces of the first shearing elements are spaced apart from each other radially. In some embodiments, the elongate tube may have a diameter of less than 5 mm.

In another aspect, a cutting device includes an elongate tube having a proximal end and a distal end, a first annular element at the distal end of the elongate tube, and a second annular element at the distal end of the elongate tube. The elongate tube has a central axis extending from the proximal end to the distal end. The first annular element includes at least one surface, and the at least one surface has a first shearing element. The second annular element includes at least one second surface, and the at least one second surface includes a second shearing element. The second annular element is concentric with the first annular element and rotatable about a central axis. The rotation causes the first shearing elements and the second shearing elements to pass each other.

This and other embodiments may include one or more of the following features. At least one surface can be perpendicular to the central axis. At least one surface can be parallel to the central axis. At least a portion of the at least one surface that is perpendicular can be located at the radial-most location of the first or second annular elements. The total radial length occupied by the at least one perpendicular surface can be at least 1/10, such as at least 1/5, such as at least 1/4, such as at least 1/3, such as at least 1/2 of the radius of the cutting device. The at least one surface can be spaced apart from the central axis. There can be at least two surfaces occupy different planes which are perpendicular to the central axis. There can be at least two surfaces that are on a common plane and separated by a gap. The distance between the first shearing element and the second shearing element can be less than 20 microns, such as less than 10 microns, such as less than 5 microns, such as approximately 1 micron. The first and second shearing elements can be in contact when passing each other. The shearing elements can be substantially parallel to the central axis. The distance from the shearing element to the central axis can be less than ⅞ of the radius, such as less than ¾ of the radius, such as less than ⅝ of the radius, such as less than ½ of the radius from the central axis. There can be alternating shearing elements that are perpendicular and parallel to the central axis, such as to form a stair-like profile. Each surface can have a plurality of shearing elements.

In another aspect, a cutting device includes an elongate tube having a proximal end and a distal end, a first annular element at the distal end of the elongate tube, and a second annular element at the distal end of the elongate tube. The elongate tube has a central axis extending from the proximal end to the distal end. The first annular element includes at least one first blade element. The at least one first blade element can include a first front surface and a first back surface, the first front surface including a first front shearing element, and the first back surface including a first back shearing element. The second annular element includes at least one second blade element. The at least one second blade element includes a second back surface and a second front surface. The second front surface includes a second front shearing element, and the second back surface includes a second back shearing element.

This and other embodiments can include one or more of the following features. The surfaces of the blades can be perpendicular to the central axis. The surfaces of the blades can be substantially parallel to the central axis. The first blade element can include at least one second blade element perpendicular to the first blade element. The distance between shearing elements of the first annular element and shearing elements of the second shearing elements can be less than 20 microns, such as less than 10 microns, such as less than 5 microns, such as approximately 1 micron. The shearing elements of the first annular element and the shearing elements of the second annular elements can be in contact when passing each other. The surfaces of the blades can have at least one tooth.

The disclosure of the present invention provides numerous device embodiments wherein the devices may be formed, in whole or in part, using a multi-layer, multi-material fabrication process wherein each successively formed layer comprises at least two materials, one of which is a structural material and the other of which is a sacrificial material, and wherein each successive layer defines a successive cross-section of the three-dimensional structure, and wherein the forming of each of the plurality of successive layers includes: (i) depositing a first of the at least two materials; (ii) depositing a second of the at least two materials; and (B) after the forming of the plurality of successive layers, separating at least a portion of the sacrificial material from the structural material to reveal the three-dimensional structure Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 1A-1C schematically depict side views of various stages of a CC mask plating process, while FIGS. 1D-G schematically depict a side views of various stages of a CC mask plating process using a different type of CC mask.

FIGS. 17A-17C illustrate an exemplary embodiment of a cutting device described herein.

DETAILED DESCRIPTION

Electrochemical Fabrication in General

FIGS. 1A-1G, 2A-2F, and 3A-3C illustrate various features of one form of electrochemical fabrication. Other electrochemical fabrication techniques are set forth in the '630 patent referenced above, in the various previously incorporated publications, in various other patents and patent applications incorporated herein by reference. Still others may be derived from combinations of various approaches described in these publications, patents, and applications, or are otherwise known or ascertainable by those of skill in the art from the teachings set forth herein. All of these techniques may be combined with those of the various embodiments of various aspects of the invention to yield enhanced embodiments. Still other embodiments may be derived from combinations of the various embodiments explicitly set forth herein.

Figure 2A:
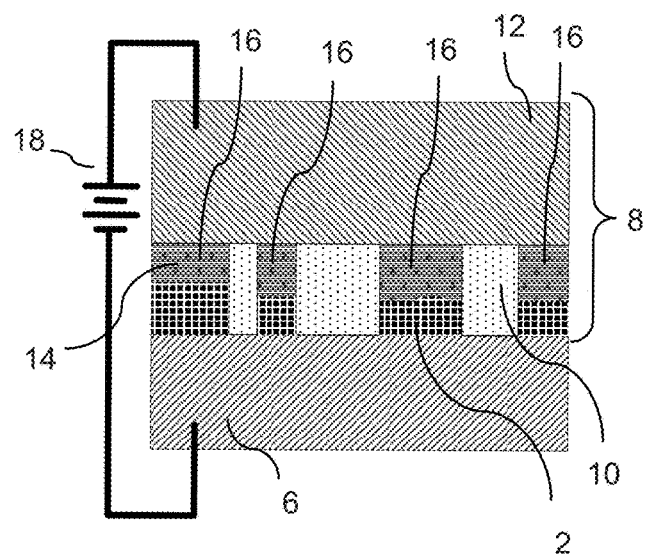
FIGS. 2A-2F schematically depict side views of various stages of an electrochemical fabrication process as applied to the formation of a particular structure where a sacrificial material is selectively deposited while a structural material is blanket deposited.
Figure 2B:
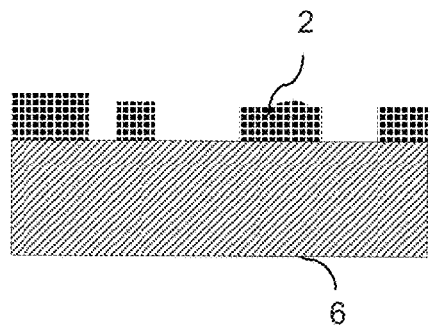
Figure 2C:
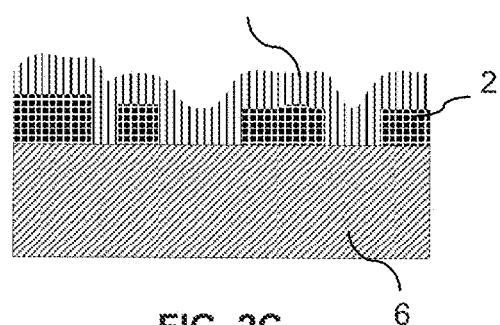
Figure 2D:
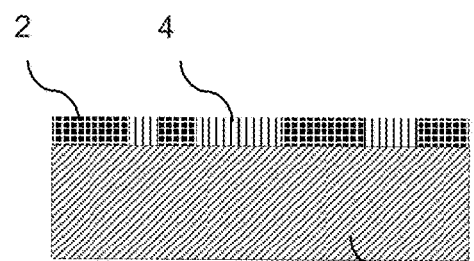
Figure 2E:
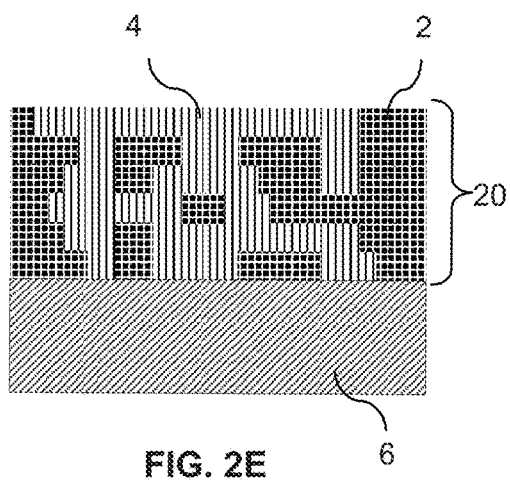
Figure 2F:
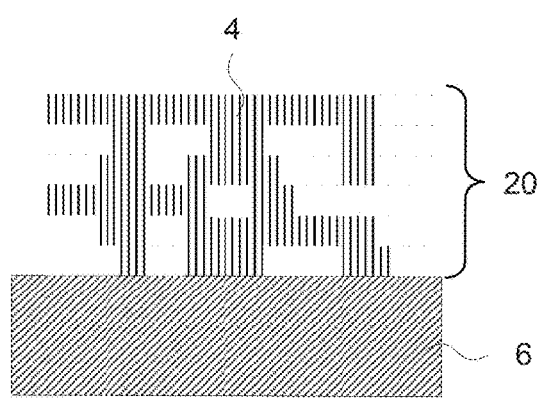
Figure 3A:
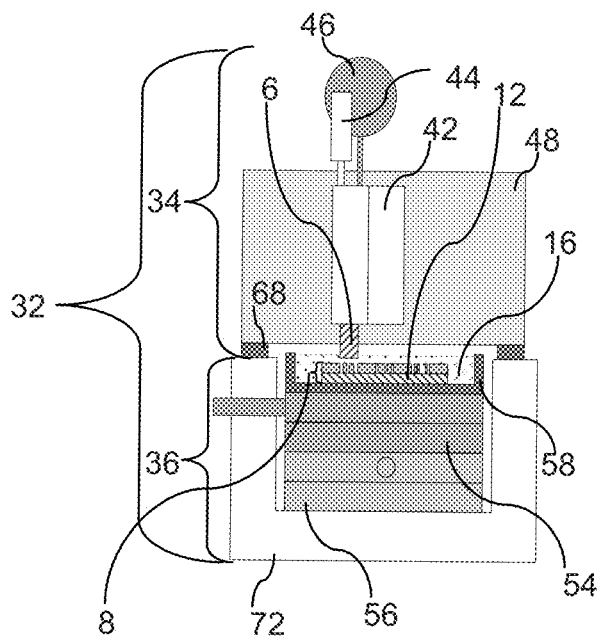
FIGS. 3A-3C schematically depict side views of various example subassemblies that may be used in manually implementing the electrochemical fabrication method depicted in FIGS. 2A-2F.
Figure 3B:
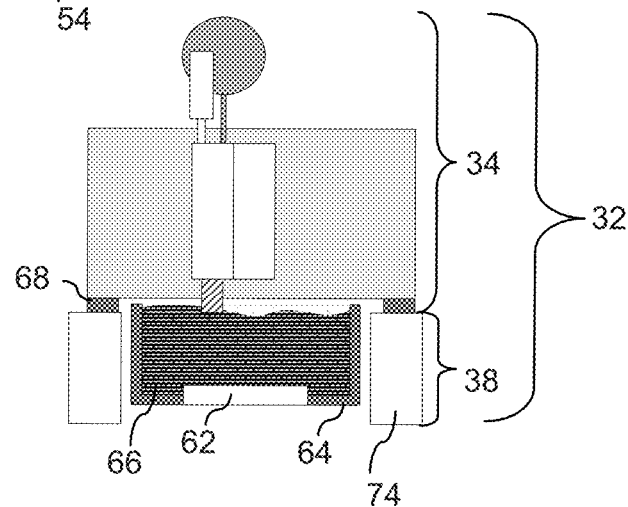
Figure 3C:
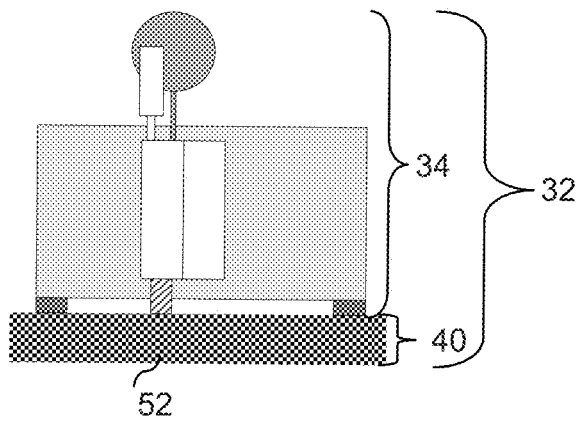
Figure 4A:
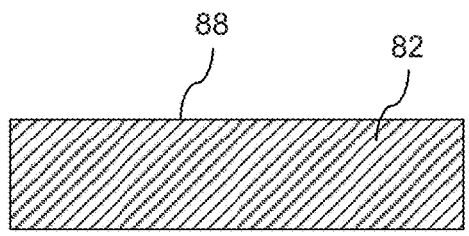
FIGS. 4A-4F schematically depict the formation of a first layer of a structure using adhered mask plating where the blanket deposition of a second material overlays both the openings between deposition locations of a first material and the first material itself
Figure 4B:
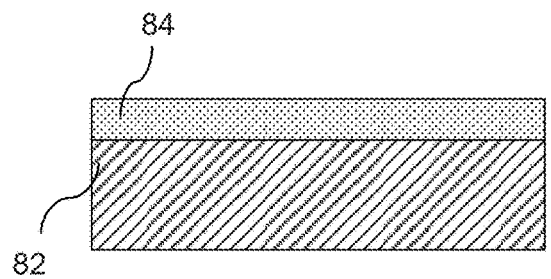
Figure 4C:
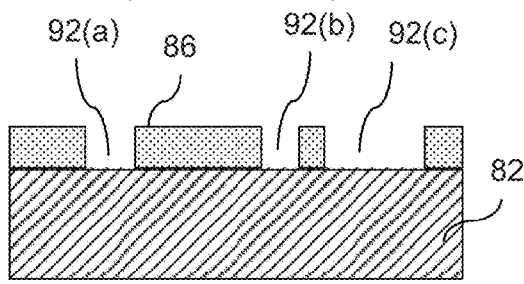
Figure 4D:
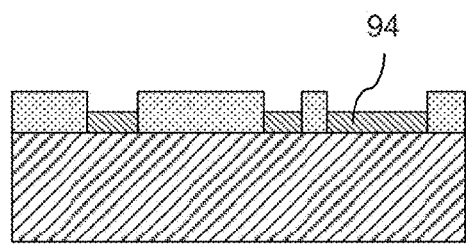
Figure 4E:
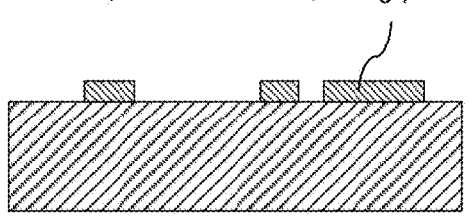
Figure 4F:
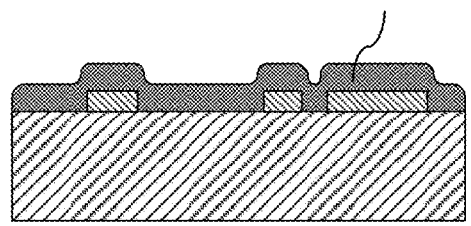
Figure 4G:
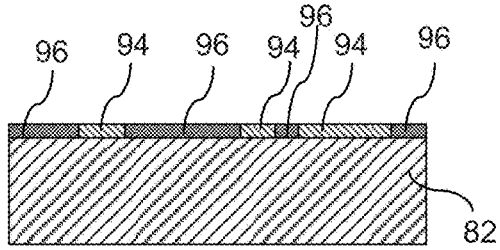
FIG. 4G depicts the completion of formation of the first layer resulting from planarizing the deposited materials to a desired level.
Figure 4H:
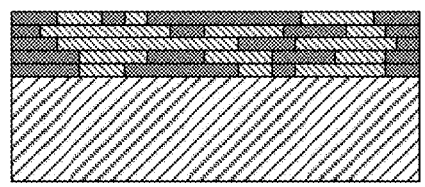
FIGS. 4H and 4I respectively depict the state of the process after formation of the multiple layers of the structure and after release of the structure from the sacrificial material.
Figure 4I:
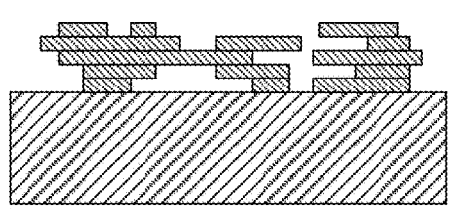

FIGS. 4A-4I illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(*a*)-92(*c*) extending from a surface 86 of the photoresist through the thickness of the photoresist to surface 88 of the substrate 82. In FIG. 4D a metal 94 (e.g. nickel) is shown as having been electroplated into the openings 92(*a*)-92(*c*). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4G several times to form a multi-layer structure are shown where each layer consists of two materials. For most applications, one of these materials is removed as shown in FIG. 4I to yield a desired 3-D structure 98 (e.g. component or device).

Various embodiments of various aspects of the invention are directed to formation of three-dimensional structures from materials some of which may be electrodeposited or electroless deposited. Some of these structures may be formed form a single build level formed from one or more deposited materials while others are formed from a plurality of build layers each including at least two materials (e.g. two or more layers, more preferably five or more layers, and most preferably ten or more layers). In some embodiments, layer thicknesses may be as small as one micron or as large as fifty microns. In other embodiments, thinner layers may be used while in other embodiments, thicker layers may be used. In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable. In the present application meso-scale and millimeter scale have the same meaning and refer to devices that may have one or more dimensions extending into the 0.5-20 millimeter range, or somewhat larger and with features positioned with precision in the 10-100 micron range and with minimum features sizes on the order of 100 microns.

The various embodiments, alternatives, and techniques disclosed herein may form multi-layer structures using a single patterning technique on all layers or using different patterning techniques on different layers. For example, Various embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Conformable contact masks, proximity masks, and non-conformable contact masks share the property that they are preformed and brought to, or in proximity to, a surface which is to be treated (i.e. the exposed portions of the surface are to be treated). These masks can generally be removed without damaging the mask or the surface that received treatment to which they were contacted, or located in proximity to. Adhered masks are generally formed on the surface to be treated (i.e. the portion of that surface that is to be masked) and bonded to that surface such that they cannot be separated from that surface without being completely destroyed damaged beyond any point of reuse. Adhered masks may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels (i.e. regions that lie within the top and bottom boundary levels that define a different layer's geometric configuration). Such use of selective etching and interlaced material deposition in association with multiple layers is described in U.S. Pat. No. 7,252,861, which is hereby incorporated herein by reference as if set forth in full.

Temporary substrates on which structures may be formed may be of the sacrificial-type (i.e. destroyed or damaged during separation of deposited materials to the extent they cannot be reused), non-sacrificial-type (i.e. not destroyed or excessively damaged, i.e. not damaged to the extent they may not be reused, e.g. with a sacrificial or release layer located between the substrate and the initial layers of a structure that is formed). Non-sacrificial substrates may be considered reusable, with little or no rework (e.g. replanarizing one or more selected surfaces or applying a release layer, and the like) though they may or may not be reused for a variety of reasons.

Definitions

This section of the specification is intended to set forth definitions for a number of specific terms that may be useful in describing the subject matter of the various embodiments of the invention. It is believed that the meanings of most if not all of these terms is clear from their general use in the specification but they are set forth hereinafter to remove any ambiguity that may exist. It is intended that these definitions be used in understanding the scope and limits of any claims that use these specific terms. As far as interpretation of the claims of this patent disclosure are concerned, it is intended that these definitions take presence over any contradictory definitions or allusions found in any materials which are incorporated herein by reference.

"Build" as used herein refers, as a verb, to the process of building a desired structure or plurality of structures from a plurality of applied or deposited materials which are stacked and adhered upon application or deposition or, as a noun, to the physical structure or structures formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519 now U.S. Pat. No. 7,252,861. This referenced application is incorporated herein by reference as if set forth in full. In most embodiments, a build layer includes at least one primary structural material and at least one primary sacrificial material. However, in some embodiments, two or more primary structural materials may be used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer boundary level). For example, lapping removes material in a substantially non-selective manner though some amount of recession one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization maybe followed or proceeded by thermally induced planarization (.e.g. melting) or chemically induced planarization (e.g. etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Supplemental structural material" as used herein refers to a material that forms part of the structure when the structure is put to use but is not added as part of the build layers but instead is added to a plurality of layers simultaneously (e.g. via one or more coating operations that applies the material, selectively or in a blanket fashion, to a one or more surfaces of a desired build structure that has been released from a sacrificial material.

"Primary structural material" as used herein is a structural material that forms part of a given build layer and which is typically deposited or applied during the formation of that build layer and which makes up more than 20% of the structural material volume of the given build layer. In some embodiments, the primary structural material may be the same on each of a plurality of build layers or it may be different on different build layers. In some embodiments, a given primary structural material may be formed from two or more materials by the alloying or diffusion of two or more materials to form a single material.

"Secondary structural material" as used herein is a structural material that forms part of a given build layer and is typically deposited or applied during the formation of the given build layer but is not a primary structural material as it individually accounts for only a small volume of the structural material associated with the given layer. A secondary structural material will account for less than 20% of the volume of the structural material associated with the given layer. In some preferred embodiments, each secondary structural material may account for less than 10%, 5%, or even 2% of the volume of the structural material associated with the given layer. Examples of secondary structural materials may include seed layer materials, adhesion layer materials, barrier layer materials (e.g. diffusion barrier material), and the like. These secondary structural materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931, now U.S. Pat. No. 7,239,219. In other embodiments, such coatings may be applied in a non-planar manner, for example, in openings in and over a patterned masking material that has been applied to previously planarized layers of material as taught in U.S. patent application Ser. No. 10/841,383, now U.S. Pat. No. 7,195,989. These referenced applications are incorporated herein by reference as if set forth in full herein.

"Functional structural material" as used herein is a structural material that would have been removed as a sacrificial material but for its actual or effective encapsulation by other structural materials. Effective encapsulation refers, for example, to the inability of an etchant to attack the functional structural material due to inaccessibility that results from a very small area of exposure and/or due to an elongated or tortuous exposure path. For example, large (10,000 µm2) but thin (e.g. less than 0.5 microns) regions of sacrificial copper sandwiched between deposits of nickel may define regions of functional structural material depending on ability of a release etchant to remove the sandwiched copper.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. Sacrificial material is typically removed via a chemical etching operation but in some embodiments may be removed via a melting operation or electrochemical etching operation. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties therefrom (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural. Sacrificial materials are typically removed by a dissolution process, or the like, that destroys the geometric configuration of the sacrificial material as it existed on the build layers. In many embodiments, the sacrificial material is a conductive material such as a metal. As will be discussed hereafter, masking materials though typically sacrificial in nature are not termed sacrificial materials herein unless they meet the required definition of sacrificial material.

"Supplemental sacrificial material" as used herein refers to a material that does not form part of the structure when the structure is put to use and is not added as part of the build layers but instead is added to a plurality of layers simultaneously (e.g. via one or more coating operations that applies the material, selectively or in a blanket fashion, to a one or more surfaces of a desired build structure that has been released from an initial sacrificial material. This supplemental sacrificial material will remain in place for a period of time and/or during the performance of certain post layer formation operations, e.g. to protect the structure that was released from a primary sacrificial material, but will be removed prior to putting the structure to use.

"Primary sacrificial material" as used herein is a sacrificial material that is located on a given build layer and which is typically deposited or applied during the formation of that build layer and which makes up more than 20% of the sacrificial material volume of the given build layer. In some embodiments, the primary sacrificial material may be the same on each of a plurality of build layers or may be different on different build layers. In some embodiments, a given primary sacrificial material may be formed from two or more materials by the alloying or diffusion of two or more materials to form a single material.

"Secondary sacrificial material" as used herein is a sacrificial material that is located on a given build layer and is typically deposited or applied during the formation of the build layer but is not a primary sacrificial materials as it individually accounts for only a small volume of the sacrificial material associated with the given layer. A secondary sacrificial material will account for less than 20% of the volume of the sacrificial material associated with the given layer. In some preferred embodiments, each secondary sacrificial material may account for less than 10%, 5%, or even 2% of the volume of the sacrificial material associated with the given layer. Examples of secondary structural materials may include seed layer materials, adhesion layer materials, barrier layer materials (e.g. diffusion barrier material), and the like. These secondary sacrificial materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931, now U.S. Pat. No. 7,239,219. In other embodiments, such coatings may be applied in a non-planar manner, for example, in openings in and over a patterned masking material that has been applied to previously planarized layers of material as taught in U.S. patent application Ser. No. 10/841,383, now U.S. Pat. No. 7,195,989. These referenced applications are incorporated herein by reference as if set forth in full herein.

"Adhesion layer", "seed layer", "barrier layer", and the like refer to coatings of material that are thin in comparison to the layer thickness and thus generally form secondary structural material portions or sacrificial material portions of some layers. Such coatings may be applied uniformly over a previously formed build layer, they may be applied over a portion of a previously formed build layer and over patterned structural or sacrificial material existing on a current (i.e. partially formed) build layer so that a non-planar seed layer results, or they may be selectively applied to only certain locations on a previously formed build layer. In the event such coatings are non-selectively applied, selected portions may be removed (1) prior to depositing either a sacrificial material or structural material as part of a current layer or (2) prior to beginning formation of the next layer or they may remain in place through the layer build up process and then etched away after formation of a plurality of build layers.

"Masking material" is a material that may be used as a tool in the process of forming a build layer but does not form part of that build layer. Masking material is typically a photopolymer or photoresist material or other material that may be readily patterned. Masking material is typically a dielectric. Masking material, though typically sacrificial in nature, is not a sacrificial material as the term is used herein. Masking material is typically applied to a surface during the formation of a build layer for the purpose of allowing selective deposition, etching, or other treatment and is removed either during the process of forming that build layer or immediately after the formation of that build layer.

"Multilayer structures" are structures formed from multiple build layers of deposited or applied materials.

"Multilayer three-dimensional (or 3D or 3-D) structures" are Multilayer Structures that meet at least one of two criteria: (1) the structural material portion of at least two layers of which one has structural material portions that do not overlap structural material portions of the other.

"Complex multilayer three-dimensional (or 3D or 3-D) structures" are multilayer three-dimensional structures formed from at least three layers where a line may be defined that hypothetically extends vertically through at least some portion of the build layers of the structure will extend from structural material through sacrificial material and back through structural material or will extend from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one or structural material or void (when the sacrificial material is removed) to the other of void or structural material and then back to structural material or void as the line is traversed along at least a portion of the line.

"Moderately complex multilayer three-dimensional (or 3D or 3-D) structures" are complex multilayer 3D structures for which the alternating of void and structure or structure and void not only exists along one of a vertically or horizontally extending line but along lines extending both vertically and horizontally.

"Highly complex multilayer (or 3D or 3-D) structures" are complex multilayer 3D structures for which the structure-to-void-to-structure or void-to-structure-to-void alternating occurs once along the line but occurs a plurality of times along a definable horizontally or vertically extending line.

"Up-facing feature" is an element dictated by the cross-sectional data for a given build layer "n" and a next build layer "n+1" that is to be formed from a given material that exists on the build layer "n" but does not exist on the immediately succeeding build layer "n+1". For convenience the term "up-facing feature" will apply to such features regardless of the build orientation.

"Down-facing feature" is an element dictated by the cross-sectional data for a given build layer "n" and a preceding build layer "n−1" that is to be formed from a given material that exists on build layer "n" but does not exist on the immediately preceding build layer "n−1". As with up-facing features, the term "down-facing feature" shall apply to such features regardless of the actual build orientation.

"Continuing region" is the portion of a given build layer "n" that is dictated by the cross-sectional data for the given build layer "n", a next build layer "n+1" and a preceding build layer "n−1" that is neither up-facing nor down-facing for the build layer "n".

"Minimum feature size" refers to a necessary or desirable spacing between structural material elements on a given layer that are to remain distinct in the final device configuration. If the minimum feature size is not maintained on a given layer, the fabrication process may result in structural material inadvertently bridging the two structural elements due to masking material failure or failure to appropriately fill voids with sacrificial material during formation of the given layer such that during formation of a subsequent layer structural material inadvertently fills the void. More care during fabrication can lead to a reduction in minimum feature size or a willingness to accept greater losses in productivity can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of sacrificial material regions. Conversely a minimum feature size for structure material regions (minimum width or length of structural material elements) may be specified. Depending on the fabrication method and order of deposition of structural material and sacrificial material, the two types of minimum feature sizes may be different. In practice, for example, using electrochemical fabrication methods and described herein, the minimum features size on a given layer may be roughly set to a value that approximates the layer thickness used to form the layer and it may be considered the same for both structural and sacrificial material widths and lengths. In some more rigorously implemented processes, examination regiments, and rework requirements, it may be set to an amount that is 80%, 50%, or even 30% of the layer thickness. Other values or methods of setting minimum feature sizes may be set.

"Sublayer" as may be used herein refers to a portion of a build layer that typically includes the full lateral extents of that build layer but only a portion of its height. A sublayer is usually a vertical portion of build layer that undergoes independent processing compared to another sublayer of that build layer.

Cylindrical Cutting Devices

Various cylindrical cutting devices or instrument embodiments will be discussed below. These devices may be used in a number of different tissue removal methods, such as planing, coring, milling, or drilling. Such tissue removal methods can be used in various applications including: (1) Disc, other tissue, or bone in the spinal region, for example, to relieve pressure on spinal nerves, (2) Ear, nose (sinus), and throat surgery, (3) ophthalmic procedures such as cataract surgery; (4) Cardiovascular (can be delivered over a guide wire) surgery or procedures such as (a) Blood clot removal (Thrombectomy); (b) Chronic total occlusion (CTO); (c) Atherectomy; (d) Removal of heart tissue; (5) Neurovascular procedures such as thrombectomy; (6) Breast surgeries or procedures such as (a) Breast duct papilloma, and (b) Lumpectomy; (7) Orthopedic surgeries and procedures such as (a) Joint surgeries; (b) Removal of bone spurs; and (c) Arthroscopic surgeries; (8) Peripheral artery disease surgeries and procedures; (9) other thrombectomy and atherectomy procedures and (10) Removal of tumors, cancerous tissue, and other excess tissue masses. The devices of various embodiments of the invention may also be used in non-medical applications.

The cutting devices described herein can advantageously be constructed using the electrochemical fabrication process. Using the electrochemical fabrication process allows the devices to be on the micrometer or nanometer scale and have precision on the order of tens of microns. Medical devices having such scale and precision are advantageous over conventional medical devices because they can be sharper, have more cutting surfaces, and be more intricately shaped. As a result, the medical devices described herein can be used for selective and accurate removal of tissue or other material within the body.

Further, using the electrochemical fabrication process is advantageous because the scale and precision available by doing so allows the medical devices to be configured to be used in conjunction with additional therapeutic or diagnostic elements. For example, the medical devices described herein may be used in conjunction with ancillary components extending through the center of the device, such as guide wires, endoscopes or other imaging methods (IVUS, OCT, OFDI, etc), aspiration, irrigation, and other micro-scale or millimeter-scale devices and instruments such as distal protection devices (see U.S. patent application Ser. No. 12/179,573), positioning instruments such as expanders (see U.S. patent application Ser. No. 12/179,573), other tissue shredding devices such as those described in U.S. patent application Ser. No. 12/490,301, and guiding and configurable elements such as those described in U.S. patent application Ser. Nos. 12/169,528; 12/179,295; and 12/144,618.

Although the medical devices described herein can be produced using the electrochemical fabrication process, additional fabrication processes may also be used.

The cutting devices described herein can each include two concentric components, which can be configured to rotate relative to one another to perform the desired surgical function. As such, only one concentric component can be rotated, both can be rotated in opposite directions, or both can be rotated in the same direction, but at different rates. The dimensions of the various cutting devices can be adjusted to obtain a desired degree of tissue removal.

Figure 5A:
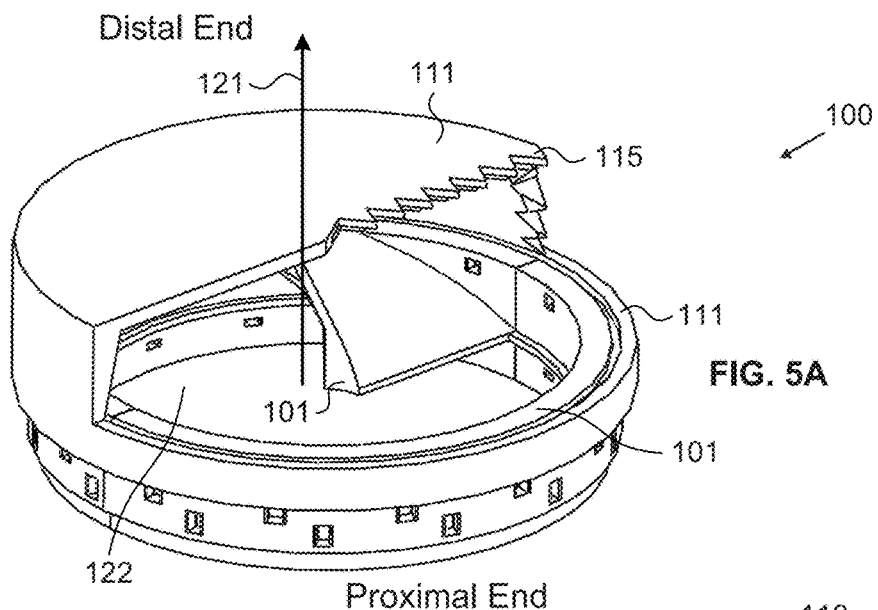
FIGS. 5A-5E illustrate an exemplary embodiment of a cutting device as described herein.
Figure 5B:
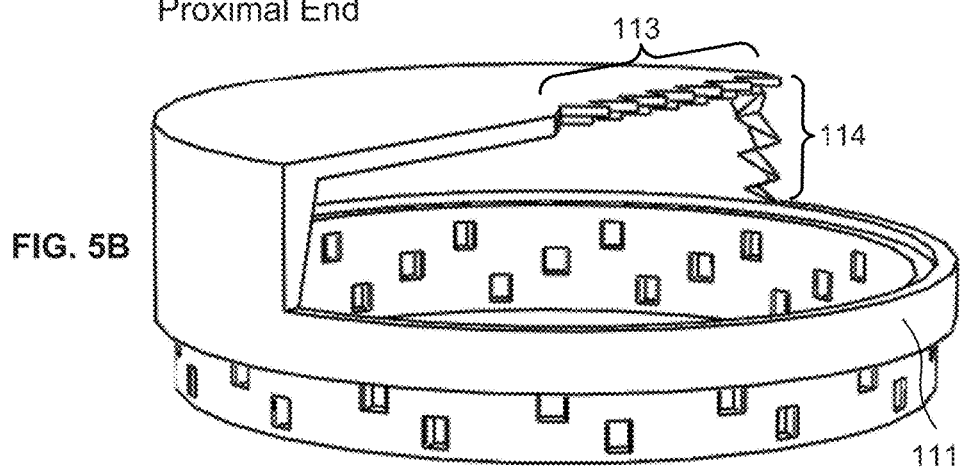
Figure 5C:
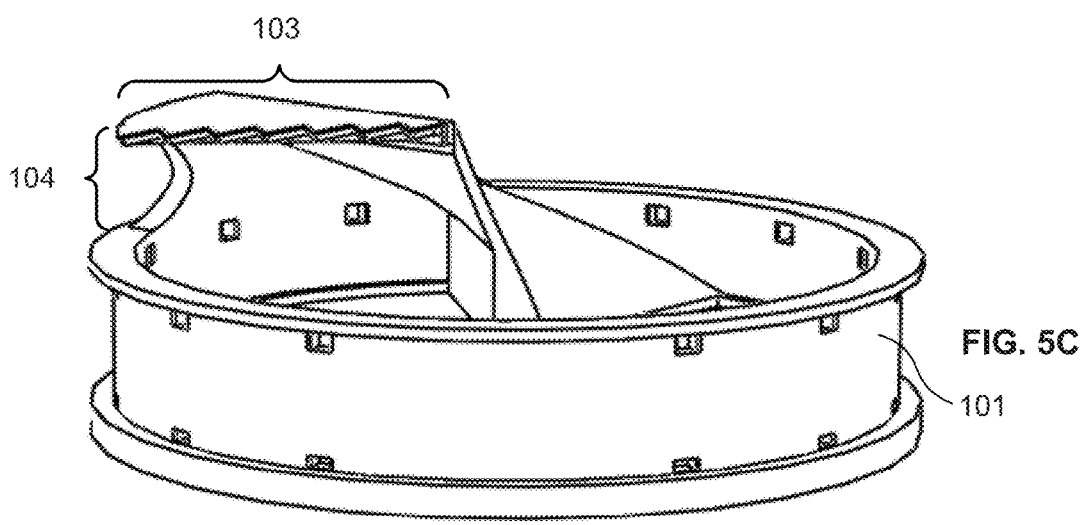
Figure 5D:
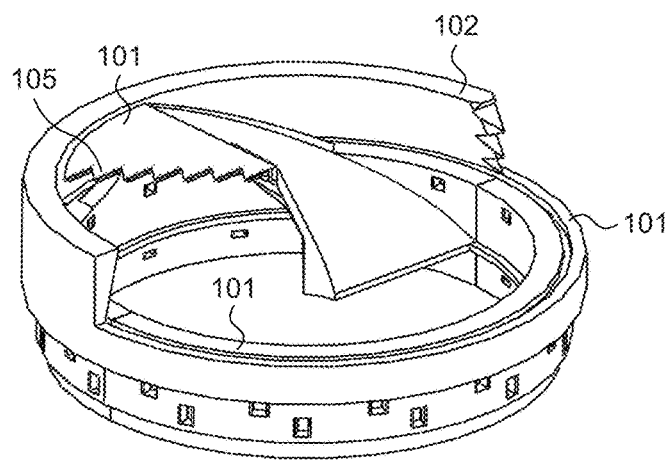
Figure 5E:
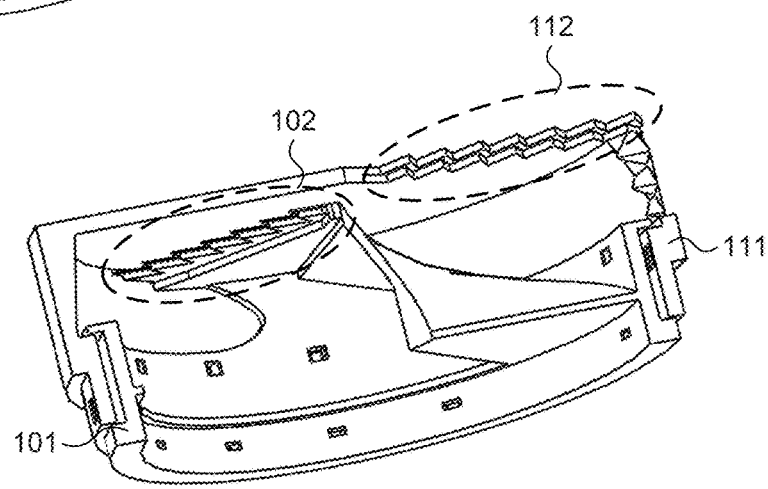

FIGS. 5A-5E illustrate a cutting device 100. The first component 101 of the device 100 includes an inner cutting element 102, having a primary cutting surface 103 and a secondary cutting surface 104. The second component 111 likewise includes an outer cutting element 112, having a primary surface 113 and a secondary surface 114. When assembled as shown in FIG. 5E, the first component 101 is capable of rotating relative to the second component 111, and the interaction of the cutting surfaces can cause shearing away of layers of tissue or other material as the inner and outer cutting elements rotate past one another. In some embodiments, either or both components can be configured to rotate in either direction. For example, the first component can rotate counter-clockwise, and the second component can rotate clockwise.

Both the inner and outer cutters 102, 112 can have singled-sided substantially radially-extending primary cutting surfaces 103 and 113 as well as secondary cutting surfaces 104 and 114 extending substantially axially at the radial extremes of the components. Having a primary cutting surface extending substantially radially and a secondary cutting surface extending substantially axially can be advantageous over prior art cutting devices because it provides more cutting surfaces for shearing off tissue. Further, the axial length of the secondary cutting surfaces 104 and 114 can be less than 100 microns, such as less than 50 microns, such as less than 10 microns. Such a small axial length allows for accurate removal of small layers of tissue, such as layers between 2 and 5 microns thick. Thus, for example, cutting device 100 can be used for planing of thin slices of tissue.

Teeth 105 and 115 can extend along the primary and/or the secondary cutting surfaces. The teeth 105 and 115 can all be configured such that they extend radially. The teeth 105 and 115 can be configured to, upon rotation of the first and second components 101, 111, engage one another substantially point-to-point, relative to a centered longitudinal axis 121 of relative rotation of the elements. The teeth 105 and 115 can aid in shearing off layers of tissue during the planing process.

As shown in the figures, the cutting surface of the first component 101 is supported by a sloped surface that sweeps a three-dimensional curve (i.e. sweeping in radial, axial or longitudinal, and azimuthal directions). The proximal facing portion of this sloped surface, when rotating in a counter-clockwise direction, may aid in pushing sheared off material in a proximal and longitudinal direction to help remove material and ensure that the cutting surface of the blade is cleared of material and ready to shear off newly encountered material.

As shown, the first component 101 of device 100 includes an intake window 122. The intake window 122 can, for example, extend across at least one-half of the distal end of the cutting device, such as approximately one-half of the distal end of the cutting device. The intake window 122 permits tissue to extend into the interior of cutting device 100 to enable the interacting cutting surfaces of the first and second components to shear the tissue, for example during a planing process.

As shown in the figures the components may be formed with a plurality of etching or release holes so that the individual components may be formed using a multi-material, multi-layer fabrication method and then the sacrificial material readily removed. In alternative embodiments, fewer, more, or even no release holes may be formed. In some embodiments, the components may be formed using an interference bushings, or with intermediate bearing elements, for example, to provide smoother operation or tighter formation tolerances. In some alternative embodiments fluid flow paths and outlets may exist between the components and may receive a fluid during operation of the device so as to provide a fluid bearing for improved device operation.

The device 100 can be a micro-scale device. Thus, the diameter of the device 100 can be less than 5 mm, such as less than 3 mm, e.g. less than 1 mm. The minimum feature size can be on the order of tens of microns, i.e. less than 100 microns, such as less than 50 microns. Moreover, the precision of the device build can be on the micron level, i.e. between 1 and 10 microns. Having a micro-scale device can advantageously allow the device to be used in small areas of the body that are unreachable by larger devices. Moreover, the precision of the build and the minimum feature size can be useful for very precise and specific tissue removal, such as planing of tissue layers of only a few microns thick. These micro-scale devices may be made using the electrochemical fabrication process described above.

Various alternatives to this embodiment are possible and include, for example, alternative blade configurations and intake configurations. For example, the teeth of the cutting elements may be made to encounter one another other than in a tip-to-tip configuration, the teeth may be removed in favor of straight blades, and the cutting blades may have cutting surfaces that have lengths which extend not just radially but also have an azimuthal component of length as well. In some embodiments, the cutting elements may be provided with cutting surfaces to allow cutting in either direction of rotation. In some alternative embodiments, the intake opening, which is defined by the distal cap of component 111 may be made larger by decreasing the azimuthal sweep or extent of the cap or smaller by increasing the azimuthal extent of the cap. In some embodiments, different numbers of inner cutting elements may form part of the inner component (e.g. 1, 2, 3, 4, or more cutting elements), and different numbers of outer cutting elements may form part of the outer component, and in some embodiments, these numbers of inner and outer cutting elements need not match. In some embodiments, cutting elements may be contained on a single component, two components, or more than two components.

During use, the two components 101, 111 of this working end of the cutting device may have their proximal ends joined or otherwise coupled to tubes or other rotatable elements such that one component (i.e. each including its respective cutting elements) stays stationary while the other rotates, such the two components 101, 111 rotate in opposite directions, or such that the two components 101, 111 rotate in the same direction but at different rates such that they still move past one another to provide shearing. During some uses, the components 101, 111 may be made to periodically, or possibly upon input from sensors (e.g. an input indicating a stall or excess slowing of the rotation), rotate a partial rotation in reverse to provide an opportunity for additional shearing attempts. During some uses, the cutting may be accompanied by aspiration from distal to proximal end to provide enhanced transport of sheared off material. In some embodiments, aspiration may be accompanied by appropriately directed irrigation. In some embodiments, more proximally located cutting and/or transport elements can be included on the components 101, 111 to cause further maceration of the removed material or proximal transportation of the material.

In some alternative embodiments, the rotation of one or both of the concentric components may occur via one or more rotating tubes that may be located within a catheter. The tubes may be driven by rotational driving elements located at a significant distance from the working area that is being operated on (e.g. outside the body of a patient). In other embodiments, the rotating tubes or other elements may be driven by a fluid driven turbine (e.g. driven by an irrigation fluid of other fluid) that is located within the catheter or other instrumental lumen.

In some embodiments, the instrument components shown in FIGS. 5A-5E may be formed using one of the multi-layer multi-material fabrication processes set forth herein or incorporated herein by reference. In some embodiments, one of the components, or part the components may be made by one of these multi-layer multi-material fabrication process while the other component or component portions may be made by one or more different processes. In still other embodiments, both of the components may be made by processes other than multi-layer, multi-material fabrication process. For example, one or both components, or portions thereof may be made from a tube which is cut to a desired shape and then bent to a desired configuration and perhaps with portions welded or otherwise joined to maintain the created configuration.

Figure 6A:
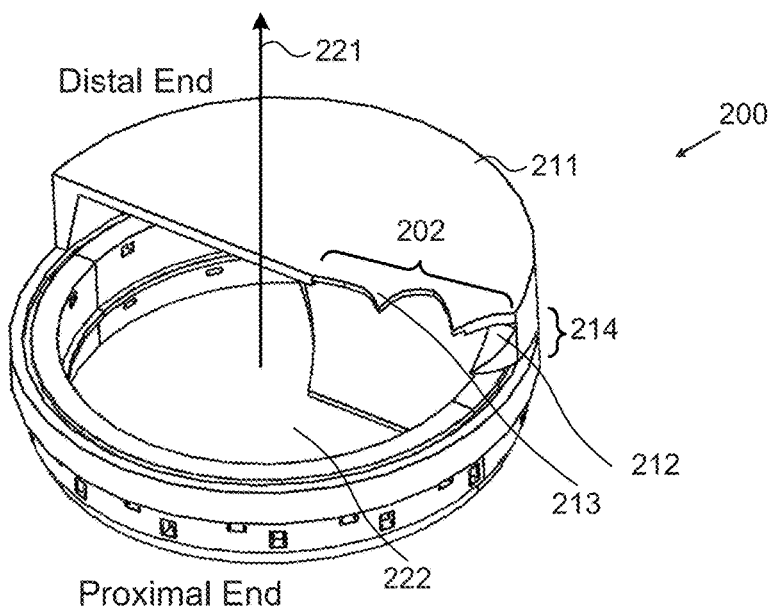
FIGS. 6A-6C illustrate an exemplary embodiment of a cutting device as described herein.
Figure 6B:
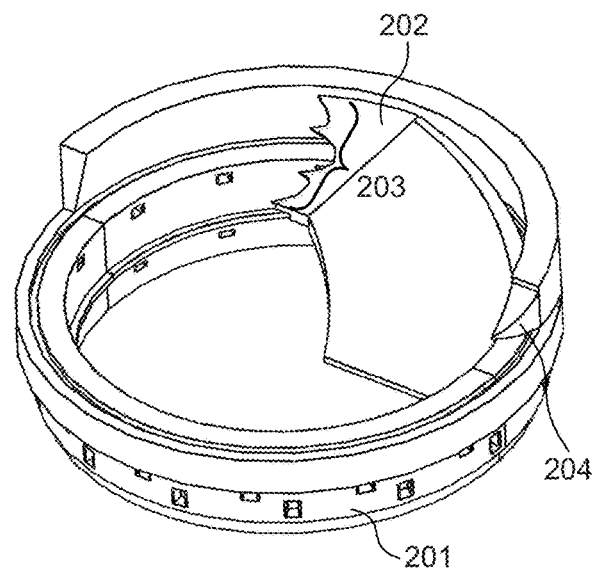
Figure 6C:
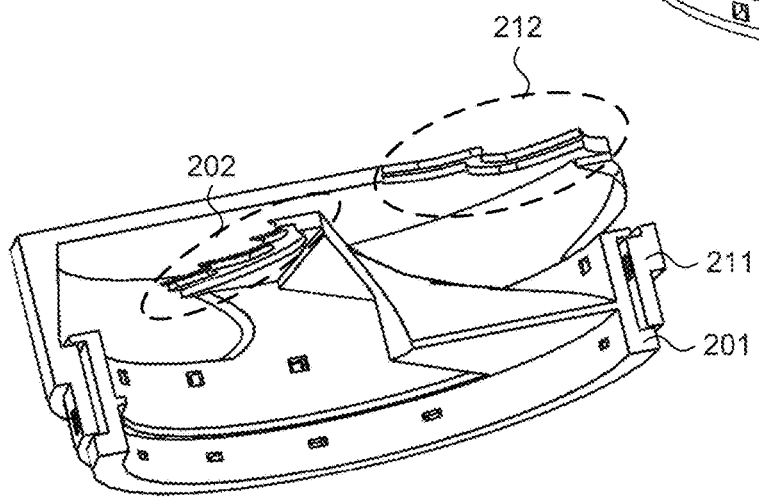

FIGS. 6A-6C provide various views of a working end of a cutting device 200. The cutting device 200 includes first and second components 201 and 211. The first component 201 includes an inner cutting element 202, having a primary cutting surface 203 and a secondary cutting surface 204. The second component 211 includes an outer cutting element 212, having a primary surface 213 and a secondary surface 214. One or both of the first and second components 201, 211 is capable of rotating about a central longitudinal axis 221 to cause relative rotation with respect to one another. The interaction of cutting surfaces 203 and 204 with cutting surfaces 213 and 214, respectively, during such relative rotation can cause shearing away of tissue or other material as the inner and outer cutting elements rotate past one another.

Both the inner and outer cutters 202, 212 can have singled-sided radial extending, and slightly azimuthal extending, primary cutting surfaces 203 and 213 as well as secondary cutting surfaces 204 and 214 extending axially at the radial extremes of the components. Teeth 205 and 215 can extend radially along the primary and/or secondary cutting surfaces.

An intake window, such as an intake window 222 of the device exists on one-half of the distal end of the cutting device 200. The intake window 222 permits tissue to extend into the interior of cutting device 200 to enable the interacting cutting surfaces of the first and second components to shear the tissue, for example during a planing process. Further, a distal cap of element 211 is located on the other half of the distal end of the cutting device 200. The cutter 200 can have many of the same advantages of the cutter 100. For example, the cutter 100 can be a micro-scale device and can have thin axially-extending cutting surfaces, allowing for access to small areas and specific and precise removal of very small layers of tissue, such as during a planing process.

Numerous variations of the cutting device 200 exist, some of which are similar, mutatis mutandis, to those noted above with regard to the first embodiment.

Figure 7A:
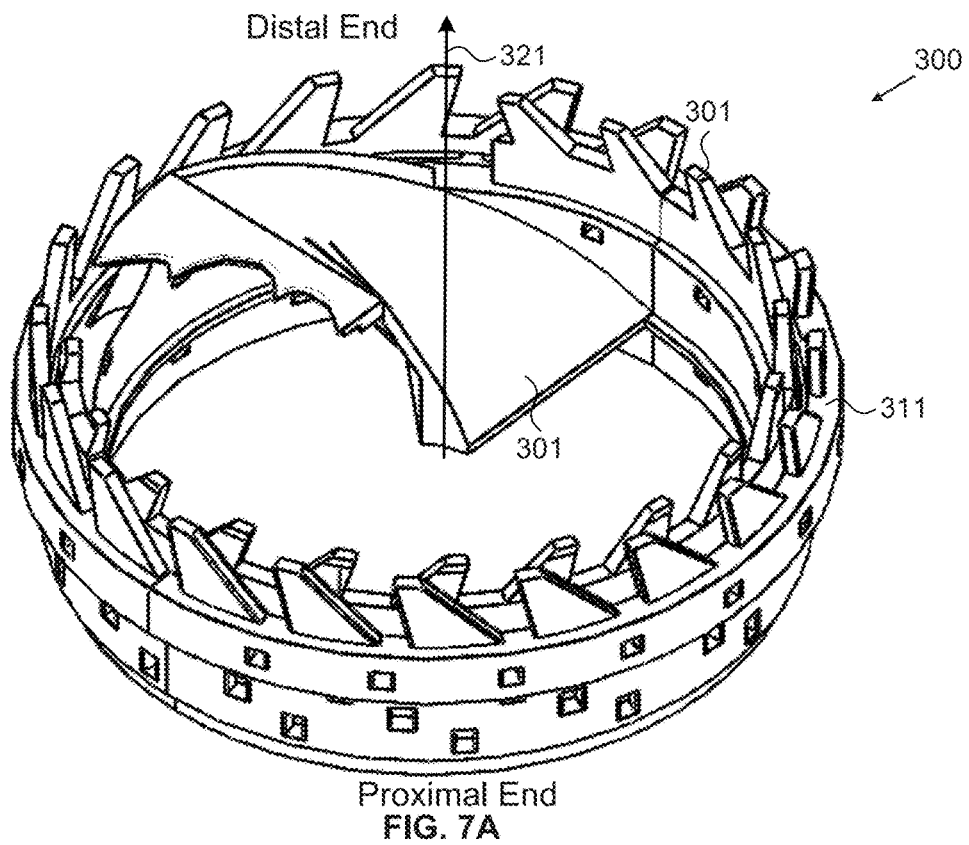
FIGS. 7A-7B illustrate an exemplary embodiment of a cutting device described herein.
Figure 7B:
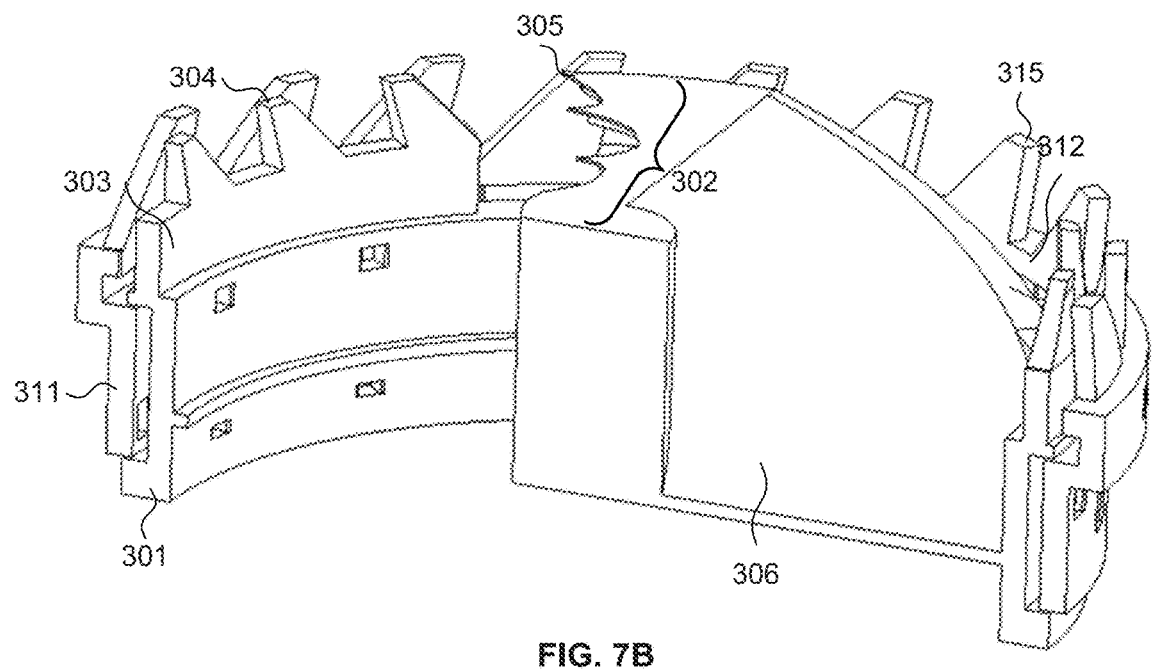

FIGS. 7A-7B provide perspective and cut views of a working end of a cutting device 300. The first component 301 of the device 300 includes an inner cutting element 302 having optional teeth 305 that extend perpendicular to the axis of rotation and a secondary peripheral cutting surface 303 with axially-extending teeth 305. The second component 311 is disposed radially outward from first element 301 and includes an outer cutting element 312 with axially-extending teeth 315. The first component 301 is capable of rotating with respect to the second component 311, which causes shearing at the periphery due to the interaction of cutting surfaces 303 and 312 while the cutting surface 302 cuts a plane of tissue. Sloped surface 306 helps draw material from the distal end of the device toward the proximal end. In some embodiments, the first component can also be configured to rotate. For example, the first component can rotate counter-clockwise, and the second component can rotate clockwise.

Both cutting surfaces 304 and 312 are provided with teeth in a crown configuration, i.e. both have teeth extending axially. The teeth can be used to drive into tissue. The teeth can have a maximum radial thickness of less than 50 microns, such as approximately 30 microns. Further, the teeth can have a pitch of less than 200 microns, such as less than 100 microns. The device 300 can be used for coring and slicing a substantially circular plane of tissue, i.e. for conducting a biopsy. The small teeth of the cutting device 300 can allow for removal of very small tissue samples, such as samples that are less than 5 microns, such as between 2 and 5 microns. Removing such small samples avoids excessive damage to surrounding tissue.

The intake window 322 of the device 300 covers nearly the entire 360 degree azimuthal region of the components to allow tissue to extend proximally into the device for shearing and easy removal of the tissue sample for analysis. The device 300 can be a micro-scale device, allowing it access to otherwise inaccessible areas of the body and may be made using the electrochemical fabrication process described above.

Numerous variations the cutting device 300 exist, some of which are similar, mutatis mutandis, to those noted above with regard to cutting device 100.

FIGS. 8, 9, 13, and 16 show components of devices similar to device 300, i.e., that include axially-extending teeth. Thus, the devices can include many of the same features and advantages as device 300.

Figure 8:
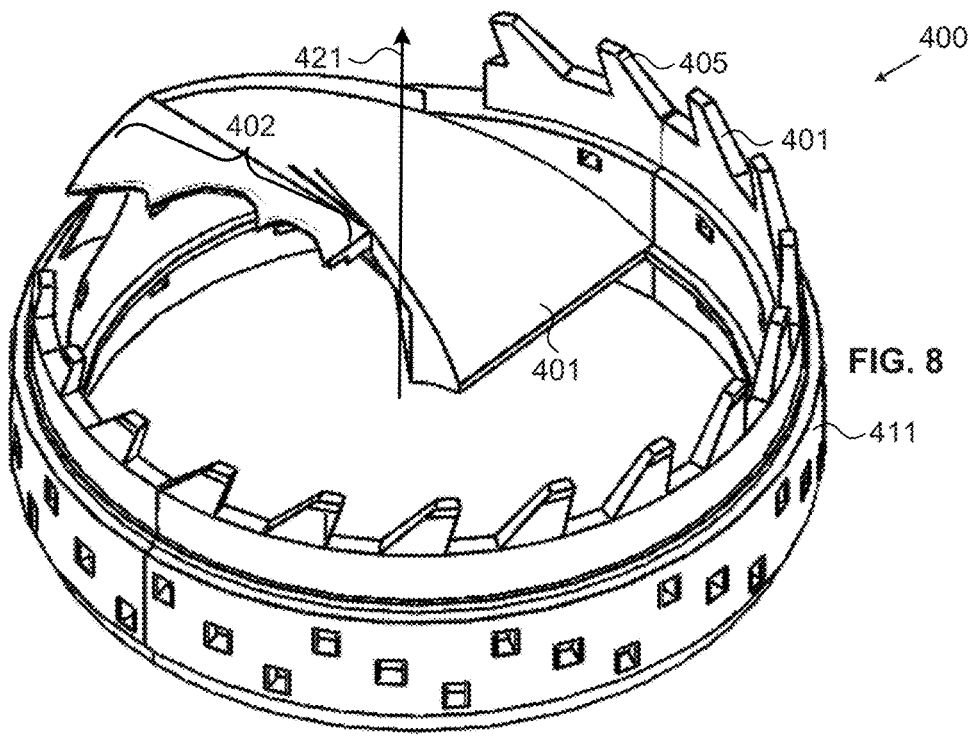
FIG. 8 illustrates an exemplary embodiment of a cutting described herein.
Figure 9:
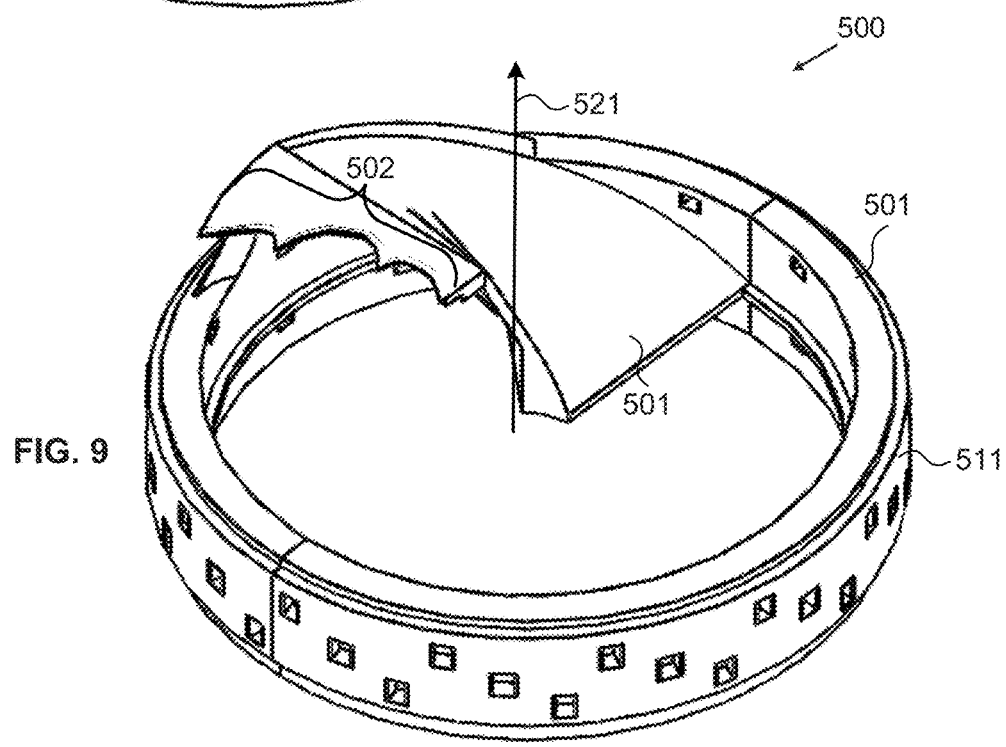
FIG. 9 illustrates an exemplary embodiment of a cutting device described herein.

FIGS. 8 and 9 are similar to the cutting device 300 with the exception that the cutter 400 (FIG. 8) has the outer crown cutting teeth removed while the cutter 500 has both the inner and out crown cutting teeth removed.

Figure 13:
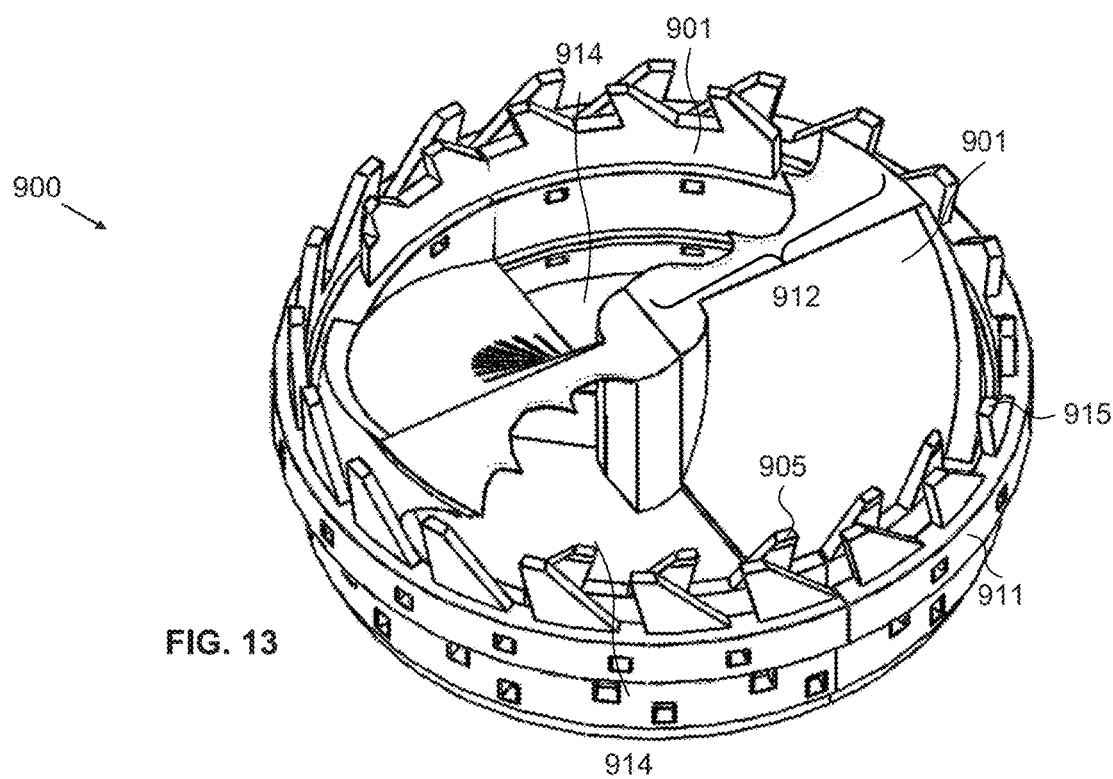
FIG. 13 illustrates an exemplary embodiment of a cutting device described herein.

FIG. 13 provides a perspective view of a working end of a cutting device 900 having first and second components 901 and 911. Similar to the other cutting devices described herein, the cutting device 900 includes teeth on each component 901, 911, respectively, that can shear against each other during rotation of one or both of the components 901, 911, to remove small pieces of tissue. Unlike the embodiment of FIG. 7, the first component 901 of the embodiment of FIG. 13 has two cutting elements 912 and two intake windows 914 for drawing in and removing tissue.

Figure 16:
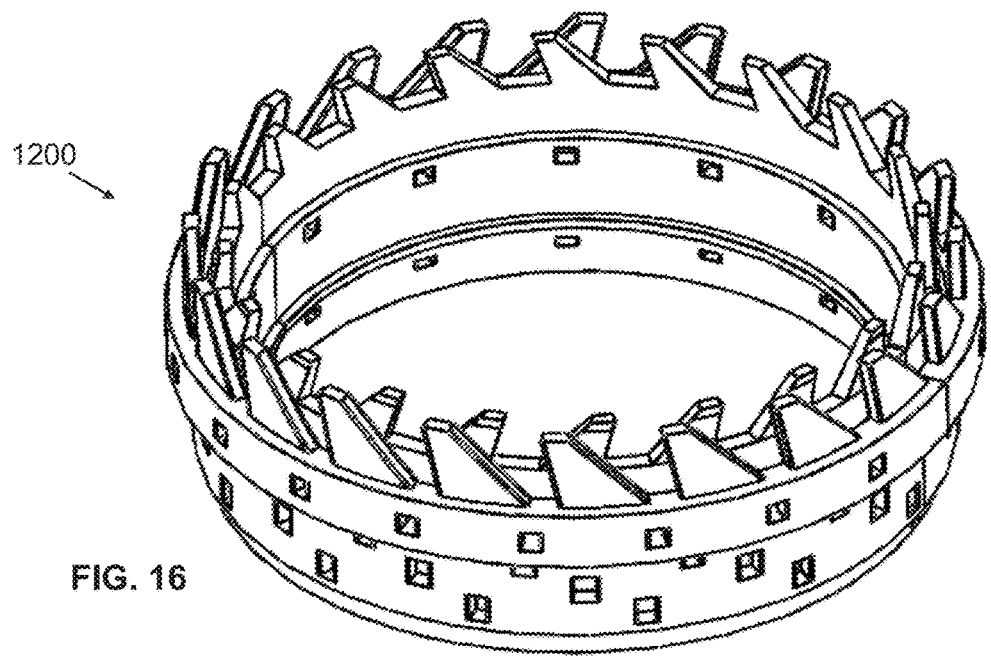
FIG. 16 illustrates an exemplary embodiment of a cutting device described herein.

FIG. 16 provides a perspective view of a working end of a cutting device 1200 having first and second components 1201 and 1211. The device includes inner and outer crown cutters having teeth 1205 and 1215 extending substantially axially. The teeth 1205 are configured to bore into a material without any additional cutting elements. This embodiment omits the inner cutting element of the first component shown in FIG. 7.

Numerous variations on these embodiments are possible and include those, mutatis mutandis, set forth regard to any of the other embodiment set forth herein.

Figure 10A:
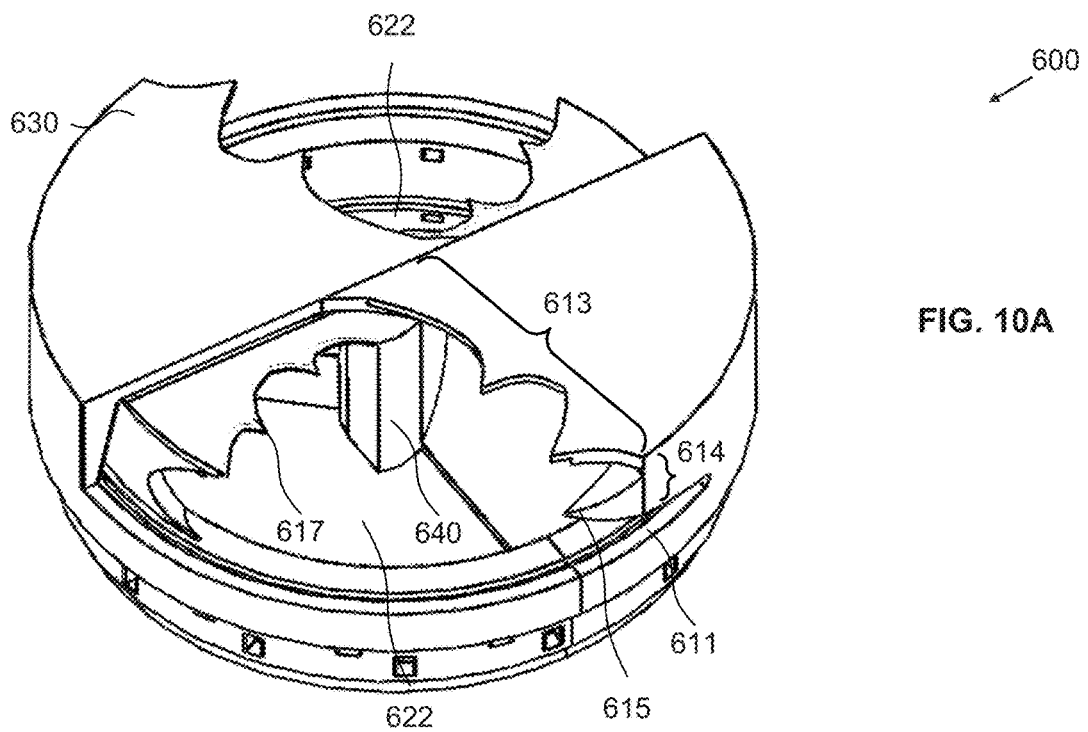
FIGS. 10A-10B illustrate an exemplary embodiment of a cutting device described herein.
Figure 10B:
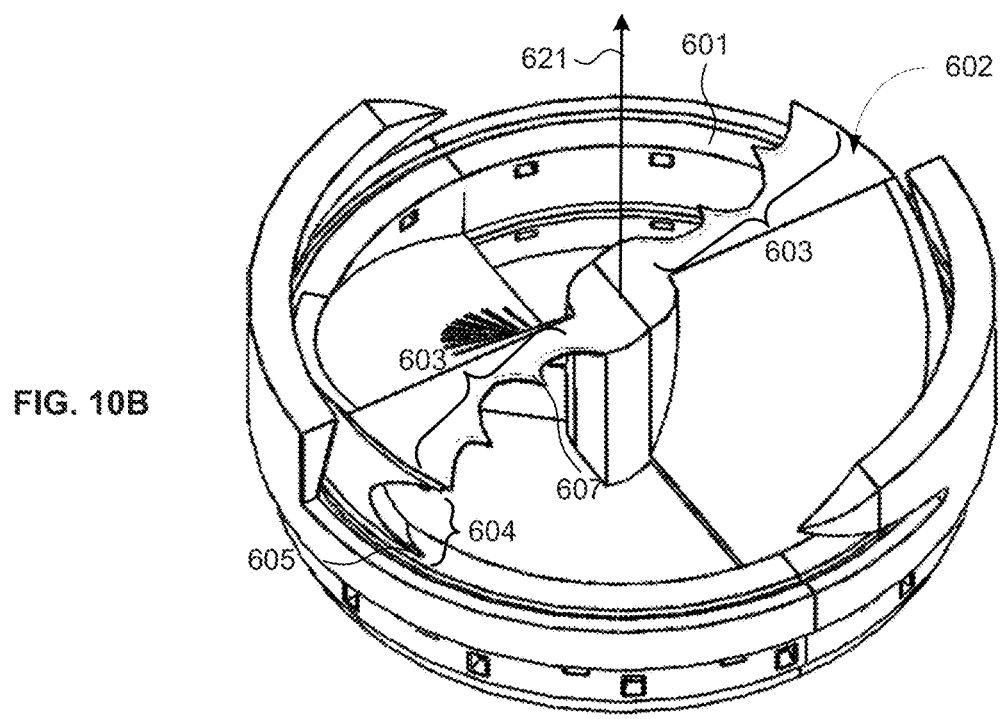

FIGS. 10A-10B provide a perspective and a perspective cut view respectively of a working end of a cutting device 600. The cutting device 600 includes first and second components 601 and 611 attached to a central shaft 640. The first component 601 includes an inner cutting element 602, having two primary cutting surfaces 603 and two secondary cutting surfaces 604. The second component 611 includes two outer cutting elements 612, having a primary surface 613 and a secondary surface 614. When assembled, first component 601 is disposed radially inward of second component 611. The first component 601 is capable of rotating relative to the second component 611 to cause shearing away of tissue or other material as the inner and outer cutting elements rotate past one another. In some embodiments, the first component can also be configured to rotate about the central longitudinal axis 621. For example, the first component can rotate counter-clockwise, and the second component can rotate clockwise.

Both the inner and outer cutters 602, 612 have two-sided radial extending, and slightly azimuthal extending, primary cutting surfaces 603 and 613, respectively. The primary cutting surfaces 603 and 613 can include teeth 607 and 617. Moreover, both the inner and outer cutters 602, 612 have secondary cutting surfaces 604 and 614 extending axially at the radial extremes of the components, which can also include teeth 605 and 615. An intake window 622 of the device consists of two opposite facing 90 degree wedges for drawing in tissue to be sheared between the rotating cutting surfaces and two sloping surfaces for drawing the sheared tissue proximally.

Advantageously, the distal end of the cutter 600 can have a flat portion 630 that extends from the outer circumference to the radial center of the cutter 600. The flat portion 630 can have an axial thickness of less than 100 microns, such as less than 50 microns. The spatial relationships between the flat surface, the cutting elements 603 and 613 and the intake windows 622 can allow for removal of tissue along a single plane, such as during a milling process, thereby avoiding removal of unwanted tissue.

Further, the cutter 600 can be a micro-scale device. Thus, the diameter of the device 600 can be less than less than 5 mm, such as less than 3 mm, e.g. less than 1 mm. The minimum feature size (e.g., the size of teeth 605 and 615) can be on the order of tens of microns, i.e. less than 100 microns, such as less than 50 microns. Moreover, the precision of the device build can be on the micron level, i.e. between 1 and 10 microns. Having a micro-scale milling device can advantageously allow the device to be used in small areas of the body that are unreachable by larger devices. Moreover, the precision of the build and the minimum feature size can be useful for very precise and specific tissue or material cutting. For example, tissue having a diameter of less than 5 microns, such as between 2 and 5 microns, can be removed during a milling process. Removing such small pieces avoids excessive damage to surrounding tissue. These micro-scale devices may be made using the electrochemical fabrication process described above.

Numerous variations of the cutter 600 exist, some of which are similar, mutatis mutandis, to those noted above. Additional variations may include the removal of the central rod shaft or the hollowing out of the shaft to form a ring element through which a guide wire, imagining device or other component may extend. In still other embodiment variations, the central rod may be a hollow shaft with perforation and may be connected to a proximal tube (e.g. with a rotatable coupling) that allows a flow of an irrigation fluid to be directed into the working region e.g. for aspiration along with removed material.

FIGS. 11, 12, 14, 15, 17, 23, 25 show similar devices to device 600, i.e., that include two rotating portions having flat distal surfaces. Thus, the devices can include many of the same features and advantages as device 600 and may be made using the electrochemical fabrication process described above.

Figure 11A:
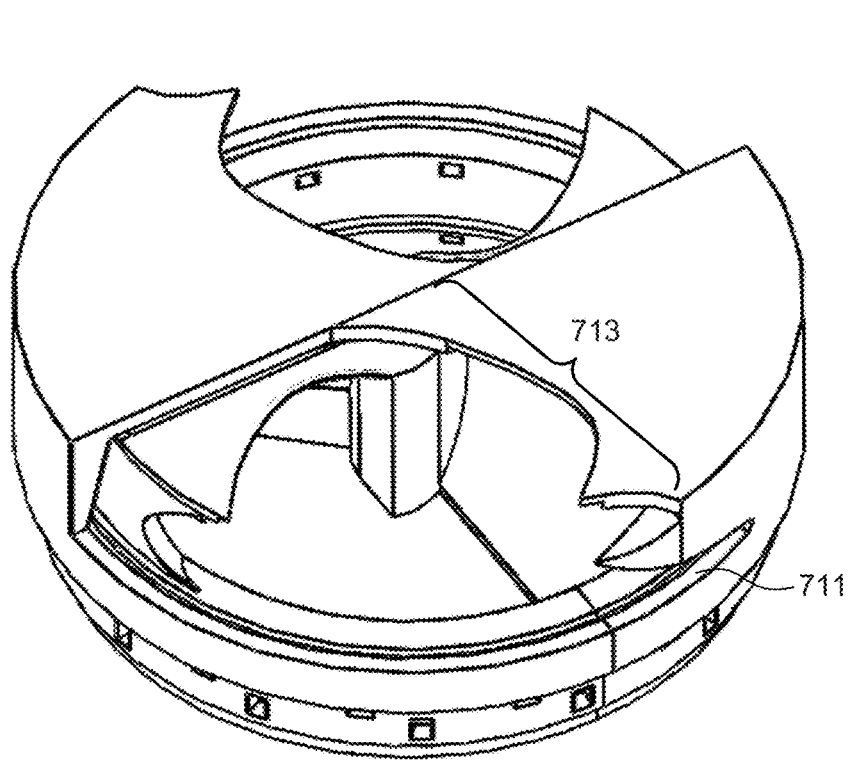
FIGS. 11A-11B illustrate an exemplary embodiment of a cutting device described herein.
Figure 11B:
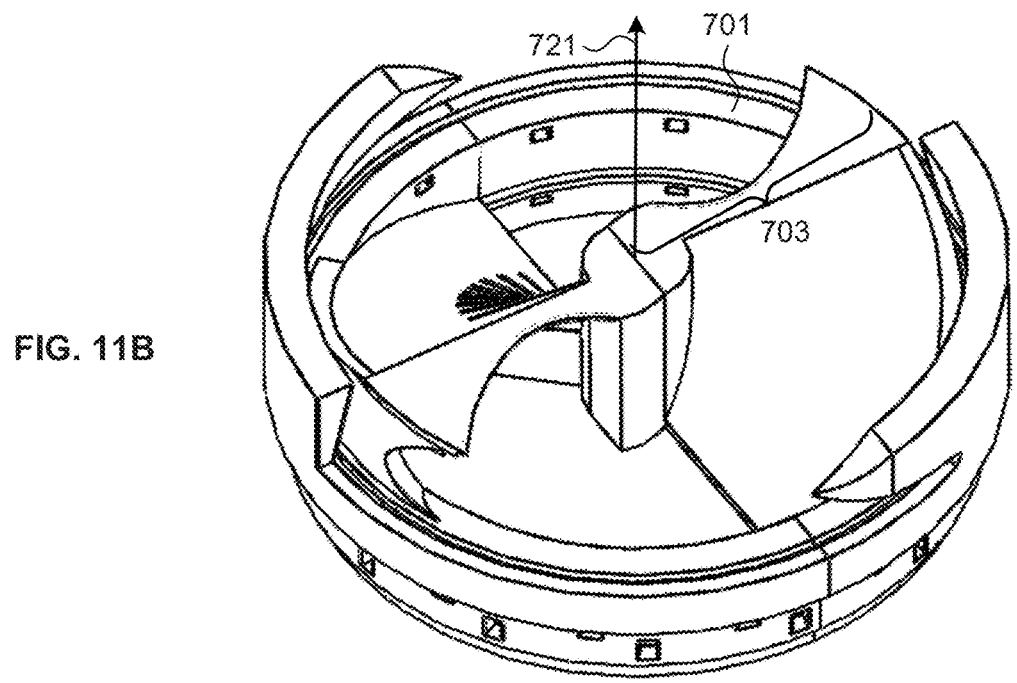

FIGS. 11A and 11B provide a perspective and a perspective cut view respectively of a working end of a cutting device 700 having first and second components 701 and 711. The cutting device 700 is similar to that of cutter 600 with the exception of a different set of primary cutting blade configurations 703 and 713.

Figure 12:
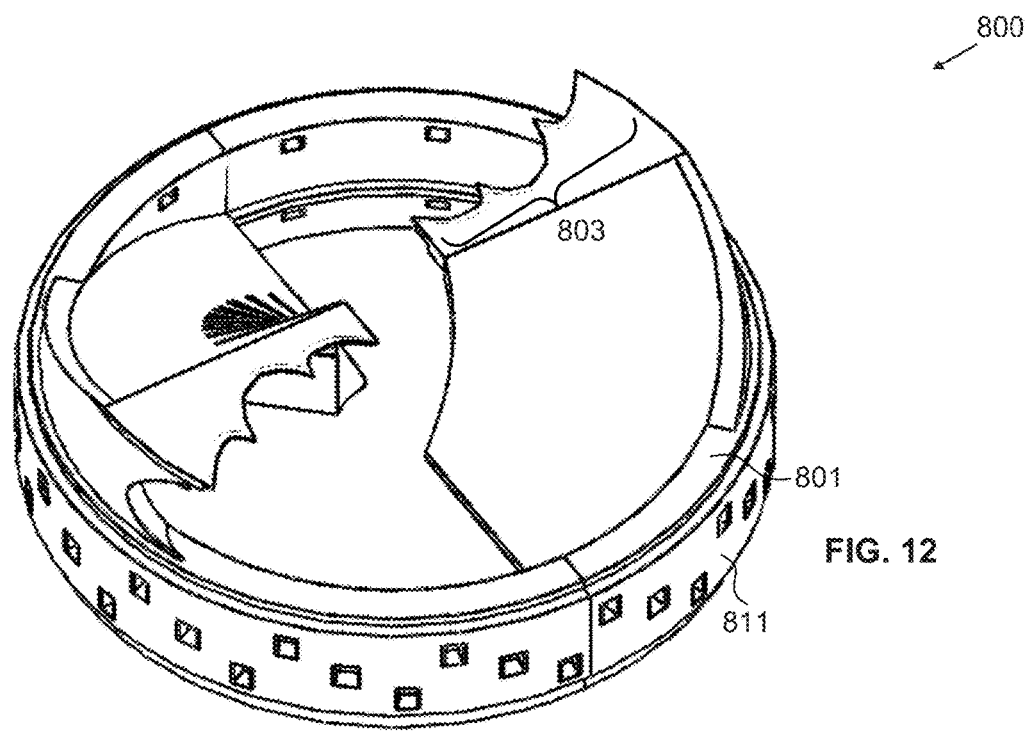
FIG. 12 illustrates an exemplary embodiment of a cutting device described herein.

FIG. 12 provides a perspective view of a working end of a cutting device 800 having first and second components 801 and 811 that are configured to be rotated with respect to each other, as in the embodiments described above. The cutting device 800 has an inner cutter similar to that of cutter 600 with the exception that the central rod or shaft is removed so that a guide wire, imaging device or other element may be extended down the central axis of the device. The device also lacks an outer cutting element. Numerous variations of cutter 800 exist some of which are similar, mutatis mutandis, to those noted above with regard to the other embodiments set forth herein above and herein after. An additional variation of the device might include the complete removal of the outer component 811 and any tube used to hold or control its motion and instead simply allow the device to extend from and rotate within a catheter or other delivery lumen.

Figure 14:
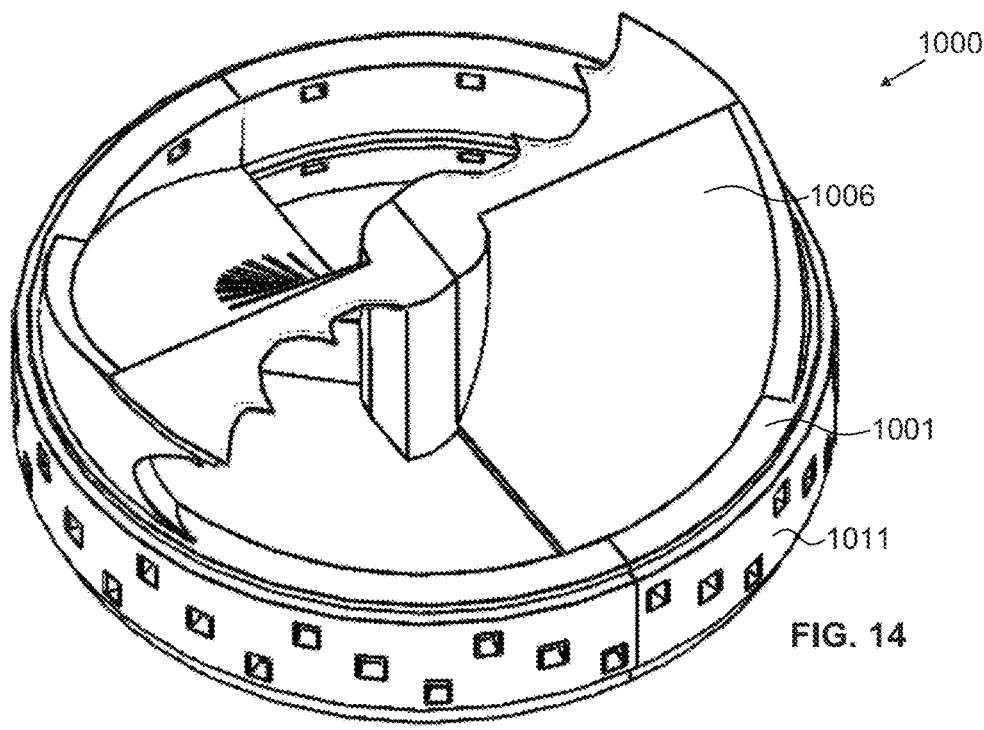
FIG. 14 illustrates an exemplary embodiment of a cutting device described herein.

FIG. 14 provides a perspective view of a working end of a cutting device 1000 having first and second components 1001 and 1011. The device has an inner cutter 1006 similar to that of cutter 600 of the invention but lacks an outer cutter. Numerous variations of cutter 1000 exist some of which are similar, mutatis mutandis, to those noted above with regard to the other embodiments set forth herein above and herein after. An additional variation of the device might include the complete removal of the outer component 1011 and any tube used to hold or control its motion and instead simply allow the device to extend from and rotate within a catheter or other delivery lumen.

Figure 15A:
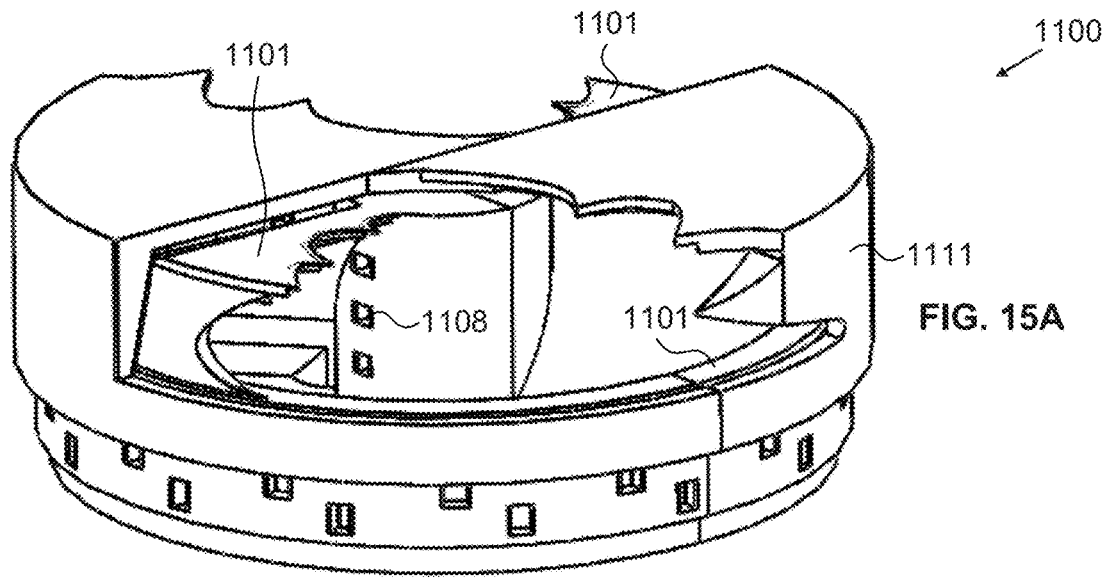
FIGS. 15A-15B illustrate an exemplary embodiment of a cutting device described herein.
Figure 15B:
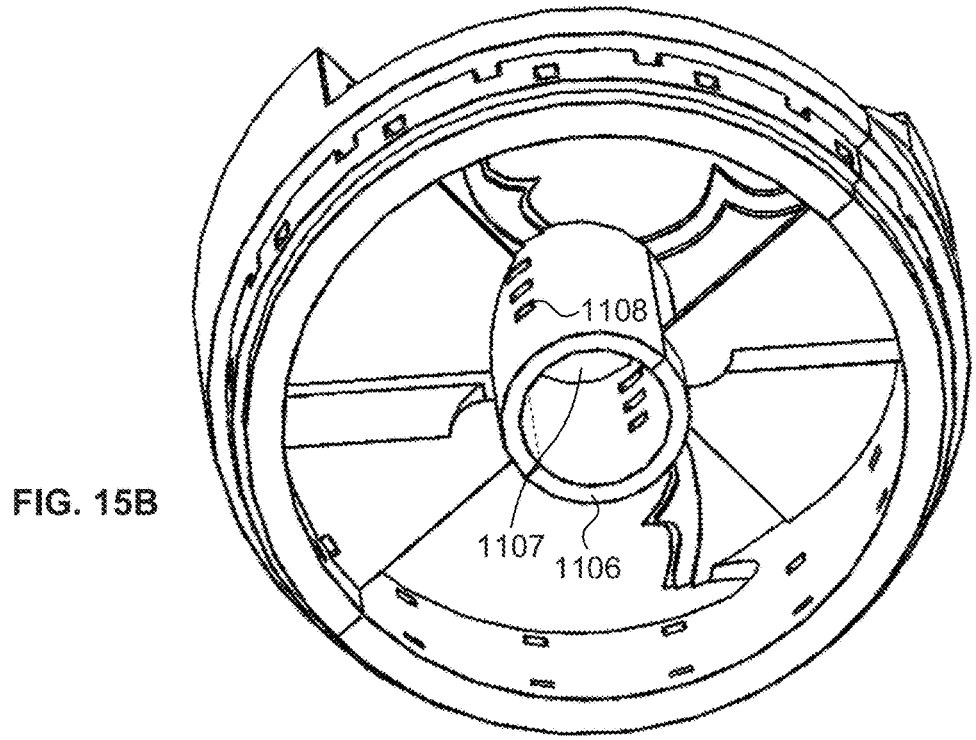

FIG. 15A-15B provide a perspective views of a working end of a cutting device 1100 having first and second components 1101 and 1111. The device is similar to that of cutter 600 except that the central shaft 1106 includes a hollow center 1107 with irrigation apertures 1108. A rotating or non-rotating tube may be connected to this central shaft to provide a flow of irrigation fluid. Numerous variations of cutter 1100 exist some of which are similar, mutatis mutandis, to those noted above with regard to the other embodiments set forth herein above and herein after. Additional variations of the device might include variations on the number, position and orientation of the apertures so that a desired flow volume and flow direction can be obtained.

FIGS. 17A-17C provide various perspective views of a working end of a cutting device 1300 having first and second components 1301, 1311. Component 1301 includes a pair of inner pinch-off cutters 1321, and component 1311 includes a pair of outer pinch-off cutters 1330. In addition, the cutting device includes a third inner component 1331. The device 1300 further includes a central irrigation tube 1306 including passage 1307 and apertures 1308 that forms part of component 1301. Relative rotation between cutters 1321 and 1331 shears tissue extending into the openings between the cutters. Component 1331 provides a tube coupler that is capable of relative rotation relative to the irrigation tube 1306 so that the feed tube can provide fluid for irrigation but need not rotate in unison with the inner cutter. The inside portion of the outer ring of the component 1301 also include inward facing aperture 1318, which may exist solely for fabrication purposes (e.g. release of sacrificial material) or may provide for additional irrigation fluid which may be supplied between a tube connecting to component 1301 and a tube connecting to component 1311. Numerous variations on this embodiment are possible and include those, mutatis mutandis, set forth regard to the various other embodiments set forth herein. Other variations might include a coupling between the irrigation tube and the inner cutting element so that these components can rotate relative to one another.

Figure 23A:
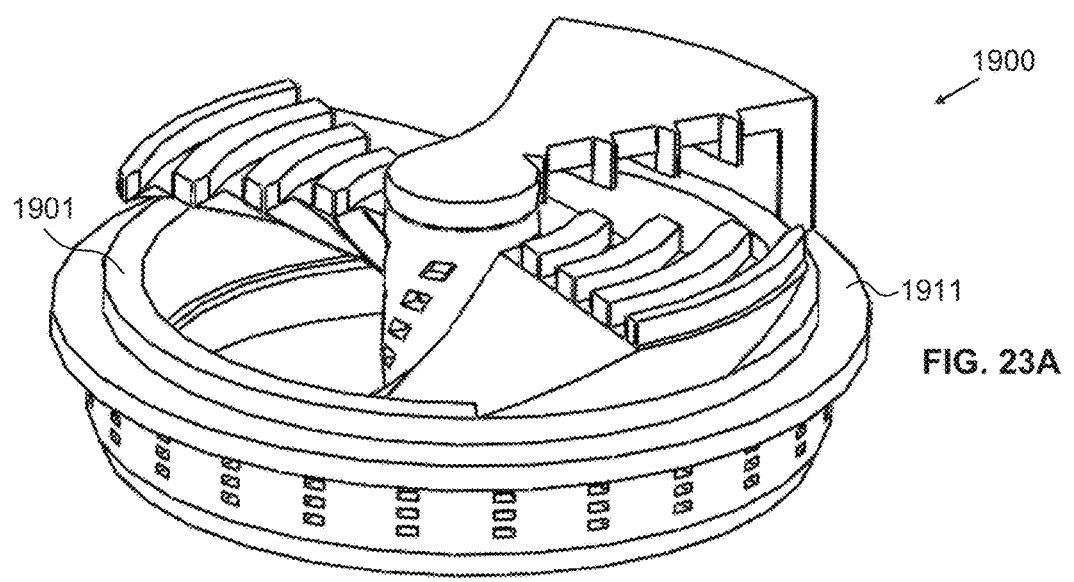
FIGS. 23A-23B illustrate an exemplary embodiment of a cutting device described herein.
Figure 23B:
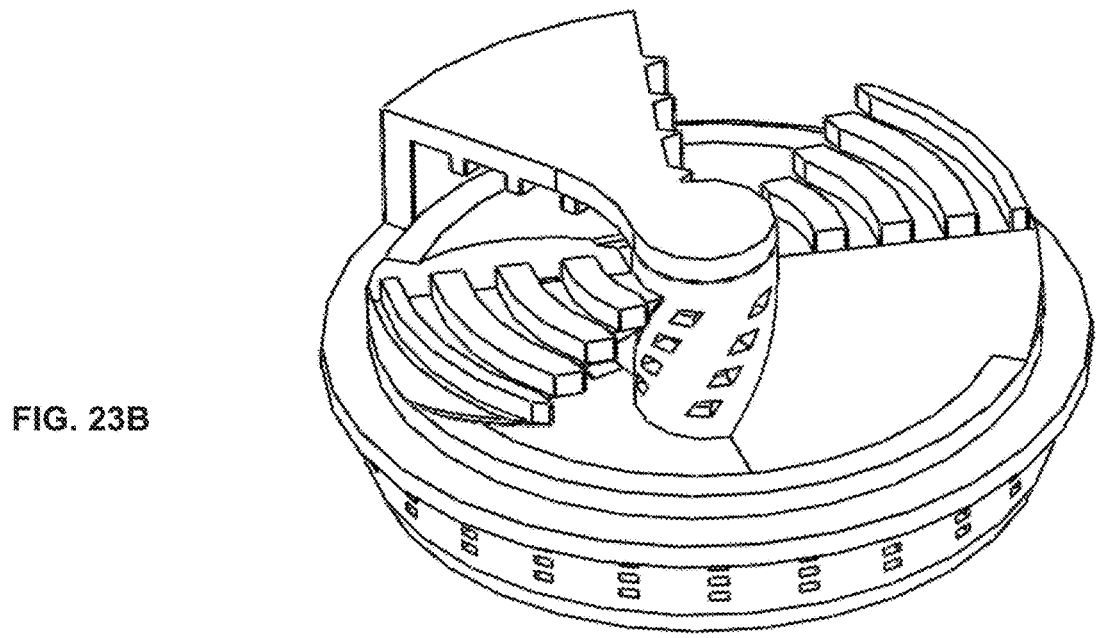

FIG. 23 illustrates several embodiments of additional cutting devices having rotating parts and a flat distal end. The embodiments shown therein have features that include various combinations or refinement of the features included in the other embodiments presented herein.

FIGS. 20A-20H provide perspective views of a working end of a cutting device 1600. The cutting device 1600 includes first and second components 1601 and 1611 which can be rotated with respect to each other. The components 1600, 1611 each include a conical cutting element 1606, 1616 extending axially. The conical cutting elements can together form a helical shape. The helical shape can be advantageous for particular medical processes, such as drilling, The edges 1620 of conical element 1616 and edges 1621 of conical element 1606 can be sharp such that the shearing action from rotation of the edges relative to one another causes the cutter 1600 to drill through material, such as tissue. Further, the edges 1620 and 1621 can have a beveled shape. The beveled edges 1620 can advantageously promote shearing. The beveled edge can have a thickness that is less than 10 microns, such as between 2 and 5 microns, allowing for precise tissue cutting.

The device 1600 also includes pairs of inner and outer cutters elements 1602 and 1612, respectively, extending axially, radially inward from ring-like base structures of components 1601 and 1611, and extending forward azimuthally, as part of components 1601 and 1611 respectively. Component 1601 also includes irrigation channels 1607 leading to irrigation apertures 1608 and 1608' on the cutting blade and on the ring-like base structure. The cutting device 1600 can be a micro-scale device such that it can be used in small areas of the body that are unreachable by larger devices, such as blood vessels having a diameter of less than 5 mm, such as less than 5 mm, such as less than 3 mm, e.g. less than 1 mm. Moreover, the precision of the build and the minimum feature size can be useful for very precise and specific tissue or material cutting. For example, tissue having a diameter of less than 5 microns, such as between 2 and 5 microns, can be removed. Removing such small samples avoids excessive damage to surrounding tissue.

Figure 20A:
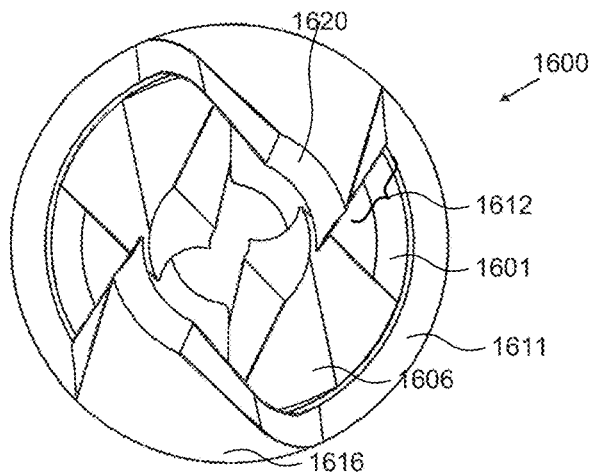
FIGS. 20A-20I illustrate an exemplary embodiment of a cutting device described herein.
Figure 20B:
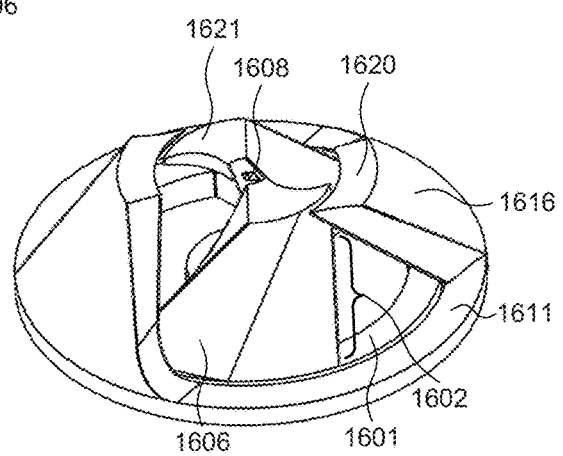
Figure 20C:
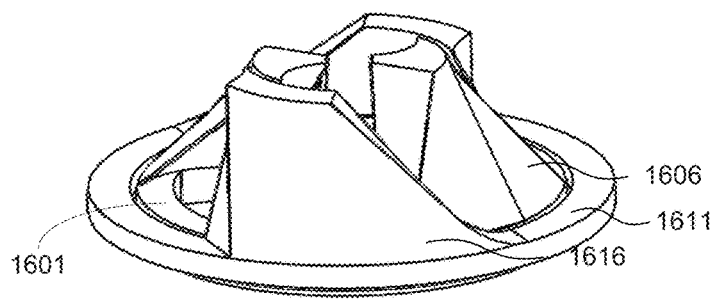
Figure 20D:
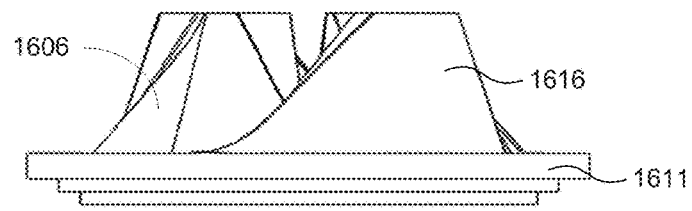
Figure 20E:
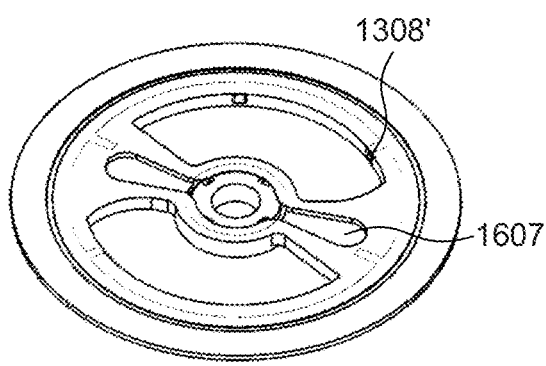
Figure 20F:
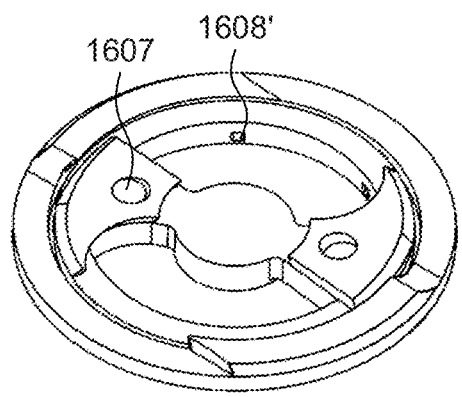
Figure 20G:
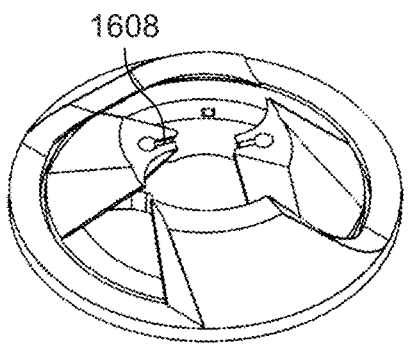
Figure 20H:
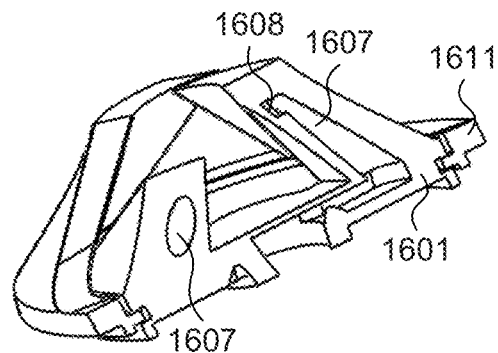
Figure 20I:
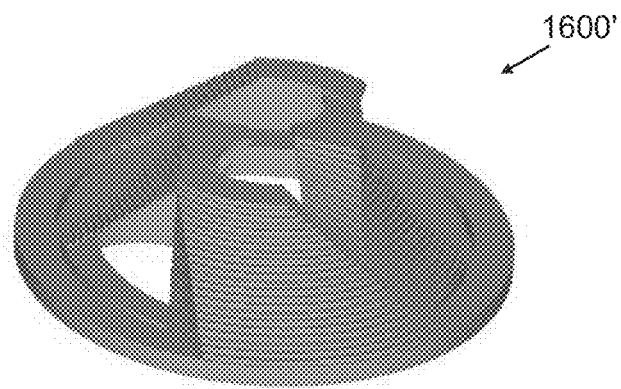

FIG. 20I provides an example layered device 1600' as the devices of FIGS. 20A-20H might be formed from a plurality of adhered layers which might be produced in a multi-layer, multi-material fabrication process (e.g. the electrochemical fabrication process described above).

Numerous variations on this embodiment are possible and include those, mutatis mutandis, set forth regard to the various other embodiments set forth herein. Other variations might include inner and/or outer blade configuration that provide for tight fitting blades while minimizing risk of tolerance based collisions by offsetting regions of initial passing (e.g. tips) radially inward (in the case of the inner cutting blades) or outward (in the case of the outer blades) in to ensure smooth passing while providing tightened ring-like base clearances or clearances on portions of the blades that are recessed from the initial contact regions. Variations of the device of this embodiment, like other embodiments described herein, can also provide for an open central region so that a guide wire, imaging device, or other tool or instrument may be moved down the center of the cutting element. The open central region may be defined by the blades themselves or by a ring like structure, with or without, a coupling element through which the central instrument may pass.

FIGS. 22 and 27 show similar devices to device 600, i.e., that include a conical-shaped distal end. Thus, the devices can include many of the same features and advantages as device 600 and may be made using the electrochemical fabrication process described above.

Figure 22A:
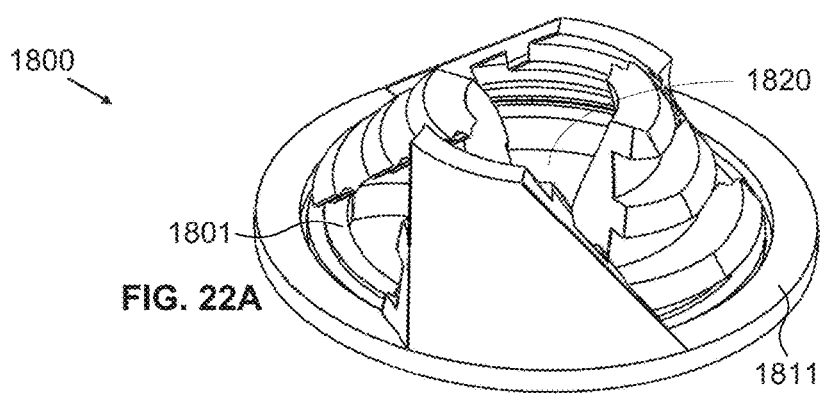
FIGS. 22A-22B illustrate an exemplary embodiment of a cutting device described herein.
Figure 22B:
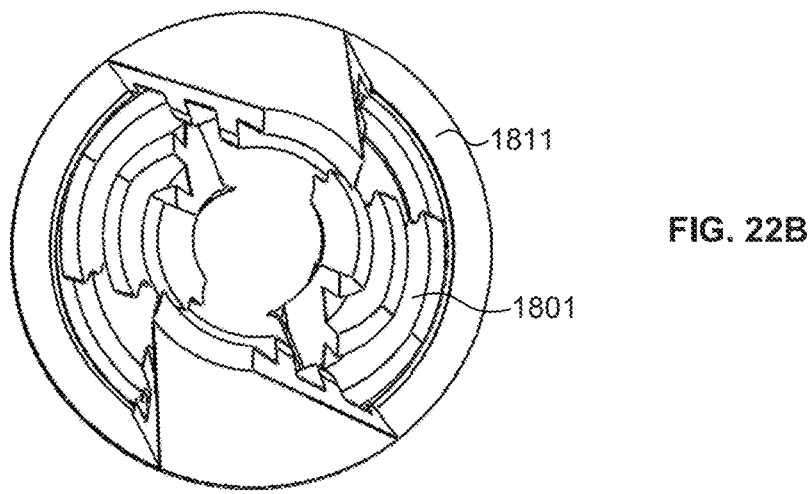

FIGS. 22A-22B provide perspective views of a working end of a cutting device 1800 having first and second components 1801 and 181. Variations of the device 1800 are similar, mutatis mutandis, to those for the other embodiments, noted herein and as with the other embodiments may include features or portions of features found only within the other embodiments themselves. Variations of the device may include a ring-like structure or structures which guide movement for an instrument inserted through the center 1820 of the cutting device so that the instrument cannot inadvertently get caught by the cutting blades themselves.

Figure 27A:
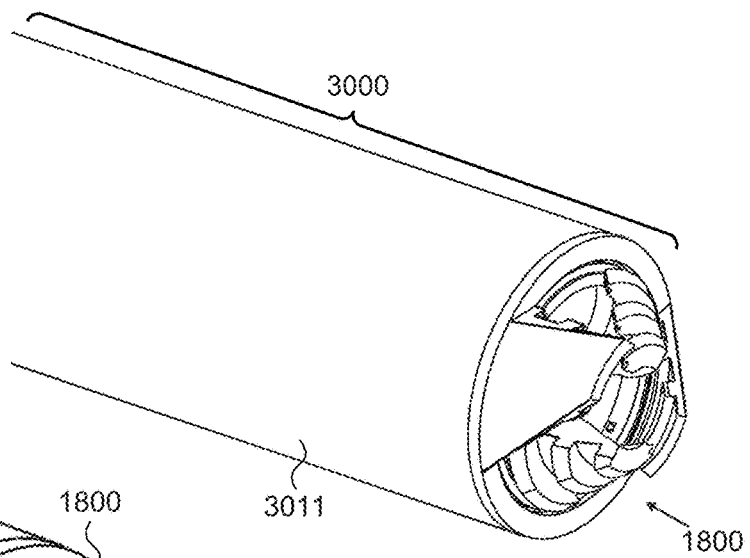
FIGS. 27A-27C illustrate an exemplary embodiment of a cutting device described herein.
Figure 27B:
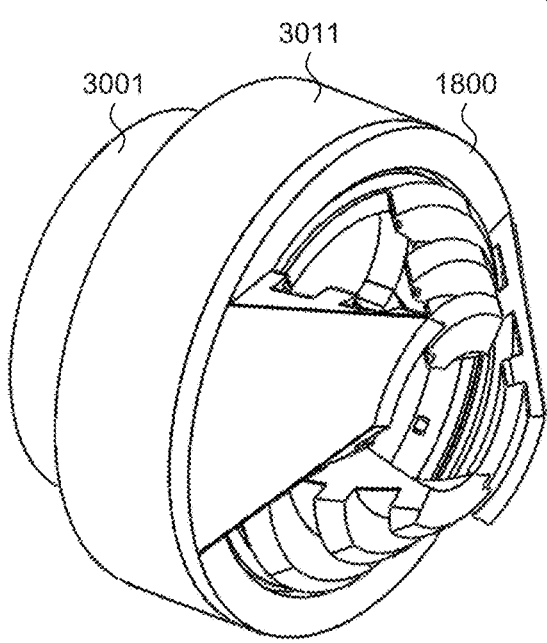
Figure 27C:
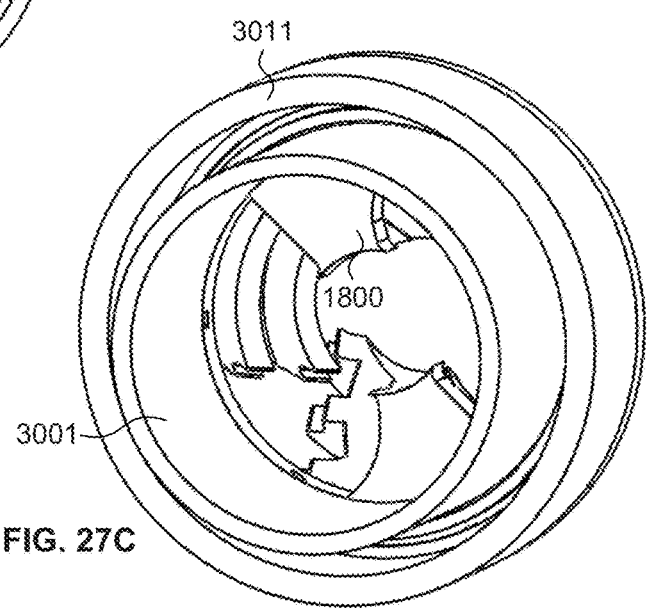

FIGS. 27A-27C provide various views of an example device 3000 including a working end of an example cutting element 1800 having its inner and outer cutting elements coupled to inner and outer tubes 3001 and 3011 respectively which can be used to rotate the cutting elements or to hold them stationary. FIGS. 27B and 27C provide truncated views of the tubes so that the inner tube may be seen. Variations of this embodiment may make use of the working ends of the other embodiments set forth herein or variations thereof. In other alternatives, the tubes or the working ends themselves may include pivot elements or bendable elements to provide a desired orientation to cutting elements when in use. Further alternatives may include the use of additional tubes or fewer tubes as appropriate. In use, various fluids or vacuum may be applied between the tubes to provide desired lubrication, irrigation, aspiration, drug delivery, or the like.

Figure 28A:
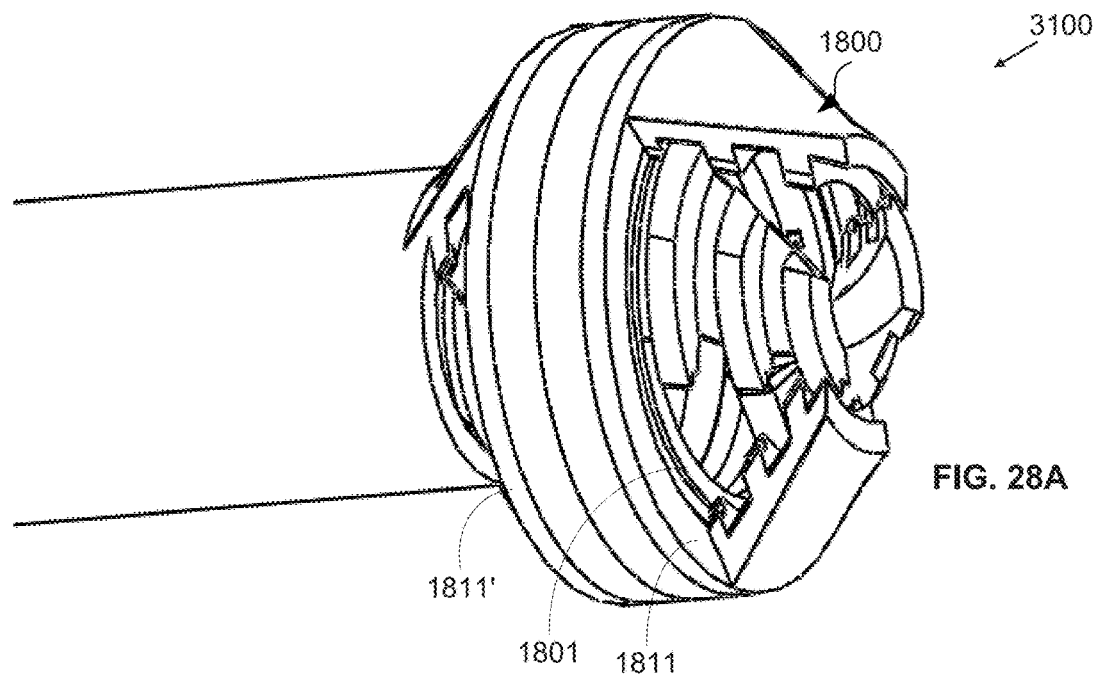
FIGS. 28A-28B illustrate an exemplary embodiment of a cutting device described herein.
Figure 28B:
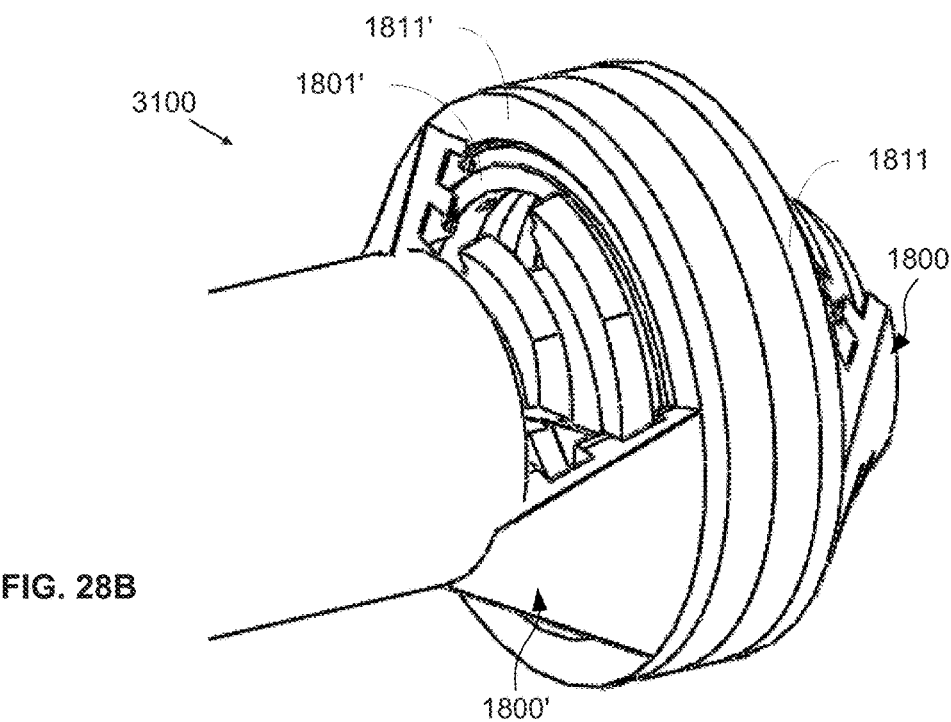

In some configurations, the cutting devices described herein can be stacked or combined to further cut tissue brought into the tube. Referring to FIGS. 28A-28B, the first device 1800 can include an inner component 1801 and an outer component 1811, which can be designed similar to any of the first and second components described herein. A second device 1800' can be combined with the first device 1800, such as stacked together axially as shown in FIGS. 28A-28B. The second device 1800' can include an inner component 1801' and an outer component 1811', which can be designed similar to any of the first and second components described herein. Optionally, as shown in FIGS. 28A-28B, the first device 1800 can be a forward-facing cutter, while the second device 1800' can be a backward-facing cutter relative to the control tubes.

Referring to FIGS. 18, 19, 21, 24, and 26, the cutting devices described herein can be configured to include multiple cutters along the axial and/or radial directions. Having multiple cutters along the axial and/or radial directions can advantageously allow for better shearing of tissue.

Figure 18:
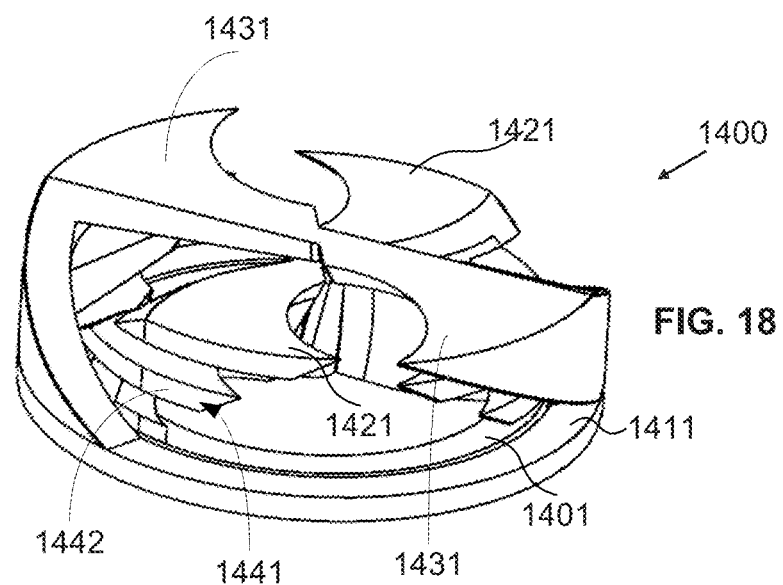
FIG. 18 illustrates an exemplary embodiment of a cutting device described herein.

FIG. 18 provides a perspective view of a working end of a cutting device 1400 having first and second components 1401, and 1411. Component 1401 includes a pair of inner pinch-off cutters 1421 spaced apart circumferentially, and component 1411 includes a pair of outer pinch-off cutters 1431 spaced apart circumferentially. The inner and outer cutting blades also include interlaced side cutters 1441 that provide for side milling. The side cutters 1441 can each include cutting surfaces 1442 that are parallel to the central axis of the cutter 600. The cutting surfaces 1442 can extend along the same radial plane. The side cutters 1441 can be spaced apart axially. Moreover, each pinch-off cutter 1421 can include a set of side cutters 1441 approximately axially aligned thereto. Further, the side cutters 1441 can each include parallel cutting surfaces 1443 extending perpendicular to the central axis of the cutter 600. The outer component 1411 can include similar cutting surfaces such that the side cutters of the inner and outer components 1401 and 1411 can interlace with one another. The axial thickness of each side cutter 1441 can be less than 100 microns, such as less than 50 microns. The interaction of the side cutters and/or the pinch-off cutters as one or both of the components 1401, 1411 rotates can allow for shearing of tissue. Numerous variations on this embodiment are possible and include those, mutatis mutandis, set forth regard to the various other embodiments set forth herein. Other variations might include different numbers of interlaced elements, different thicknesses of interlaced elements, and different interlacing depths for those elements.

Figure 19:
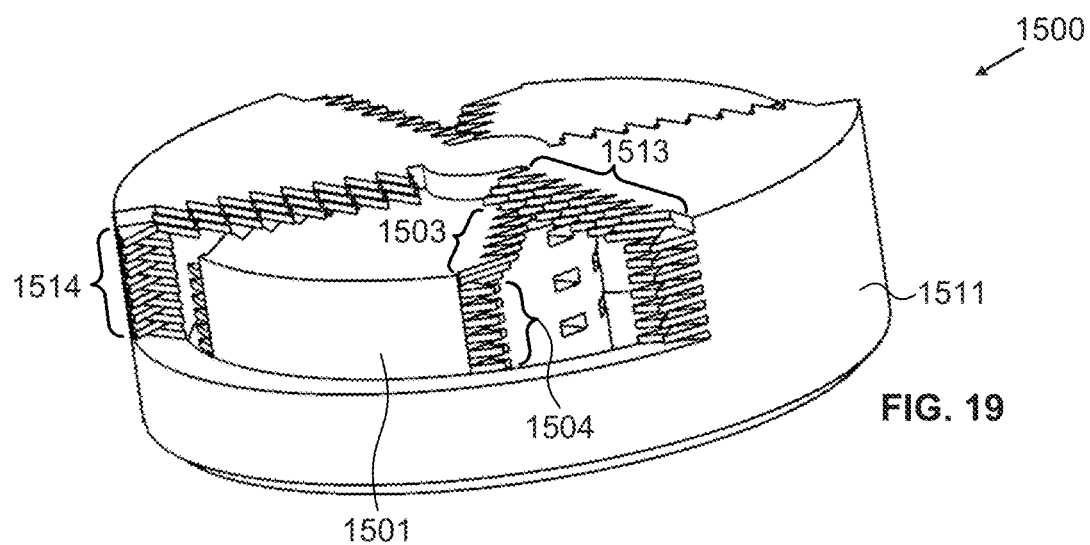
FIG. 19 illustrates an exemplary embodiment of a cutting device described herein.

As shown in FIG. 19, a cutting device 1500 can include first and second components 1501 and 1511. The device 1500 includes stacked levels of cutters 1504 on primary cutting elements of both the inner and outer components. The device 1500 further includes side teeth 1514 that provide for retention and shredding of material. The teeth of the inner and outer elements can both extend perpendicular to the central axis of the device and can be located on opposing planes so as to allow shearing when the components 1501, 1511 are rotated relative to one another. The teeth can have an axial thickness of less than 100 microns, such as less than 50 microns, such as less than 10 microns. The device 1500 can also include irrigation apertures on central shaft. Other variations might include different numbers and configurations of stacked cutter primary and secondary cutting teeth.

Figure 21:
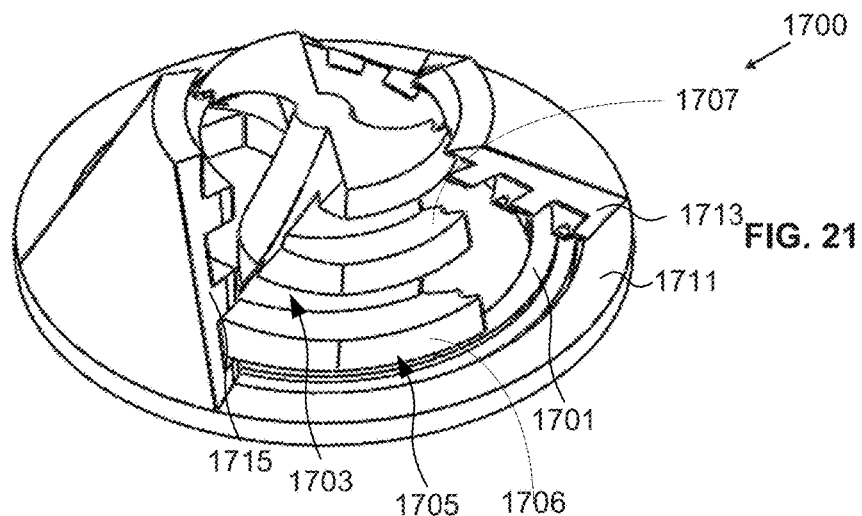
FIG. 21 illustrates an exemplary embodiment of a cutting device described herein.

FIG. 21 provides a perspective view of a working end of a cutting device 1700 having first and second components 1701, and 1711. The first component 1701 includes inner cutting blades 1703 spaced apart circumferentially, while the second component 1711 includes outer cutting blades 1713 spaced apart circumferentially. The inner cutting blades 1703 are provided with outward facing side teeth 1705 that interlace with inward facing side teeth 1715 on the outer cutting blades 1711 to shear tissue as the first and second components rotate with respect to each other. The teeth 1705 can be stacked and spaced apart axially. The teeth 1705 can each include a surface 1706 parallel to the central axis of the device and a surface 1707 perpendicular to the central axis of the device. The surfaces 1706 extending approximately parallel with each other can each be located along a different radial dimension so as to create a conical-shaped distal end of the device. Variations of the device 1700 are similar, mutatis mutandis, to those for the other embodiments, noted herein and as with the other embodiments may include features or portions of features found only within the other embodiments themselves. Variations of the device may include irrigation channels and apertures.

Figure 24A:
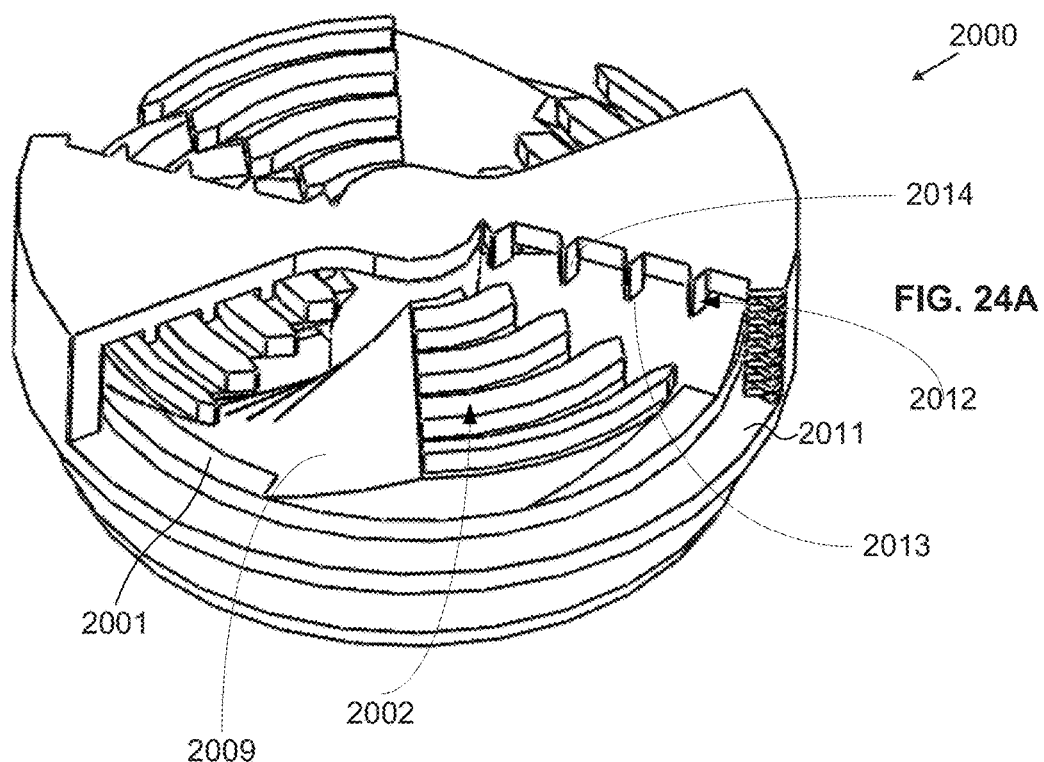
FIGS. 24A-24B illustrate an exemplary embodiment of a cutting device described herein.
Figure 24B:
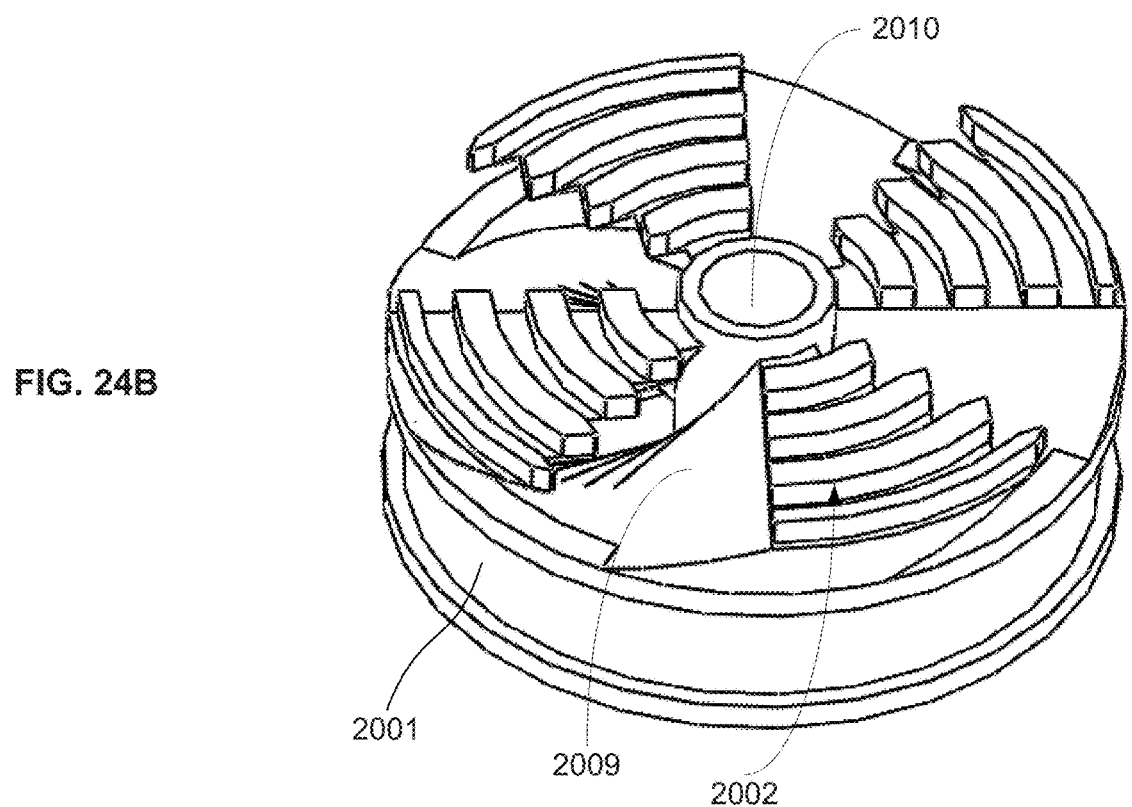
Figure 25A:
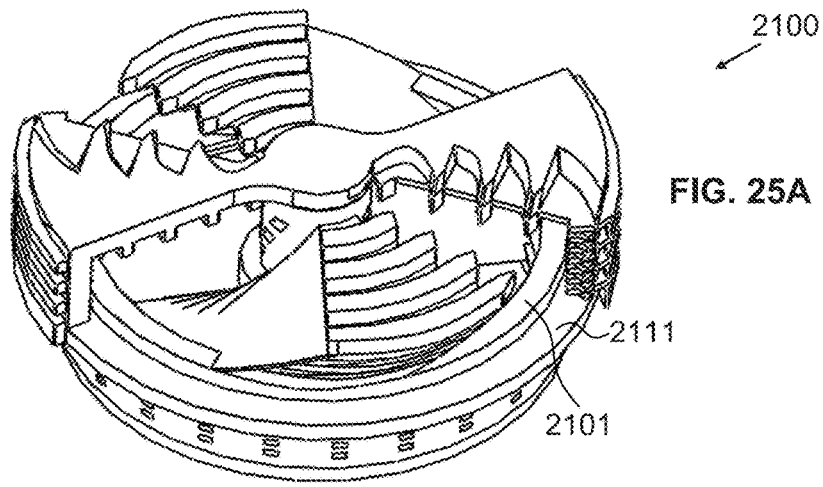
FIGS. 25A-25C illustrate an exemplary embodiment of a cutting device described herein.
Figure 25B:
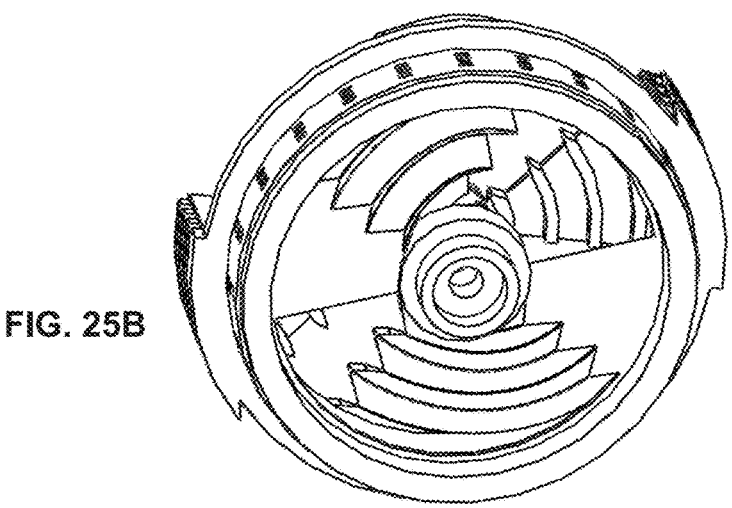
Figure 25C:
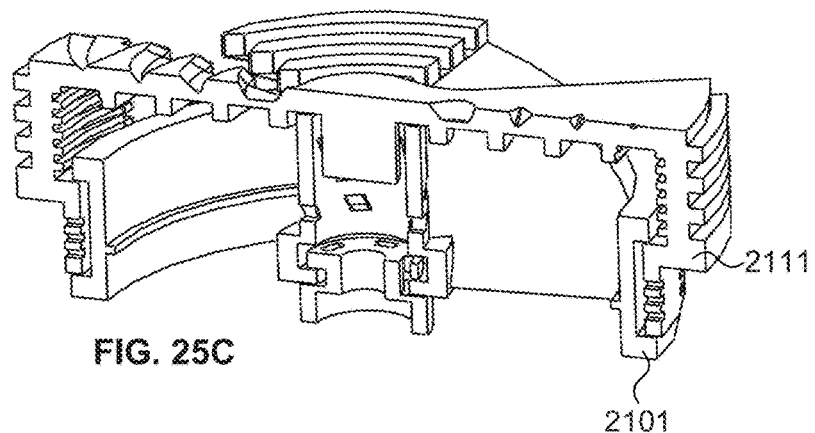

As shown in FIGS. 24A-24B, a cutting device 2000 can include an outer component 2011 and an inner component 2001. The outer component 2011 can include axially-extending cutting elements 2012. The axially-extending cutting elements 2012 can each have a cutting surface 2013 extending parallel to the central axis of the device and a cutting surface 2014 extending perpendicular to the central axis of the device. The axially-extending cutting elements can be spaced apart radially and/or circumferentially. Likewise, the inner component 2001 can include similar axially-extending elements 2002. The axially extending elements 2002 can be spaced apart radially and/or circumferentially. Further, the inner cutting element 2001 can include one or more sloped surfaces 2009 such that the inner cutting elements 2001 can be spaced apart axially. The axially-extending elements of each component can extend along a common axial plane. The interaction of the surfaces of the cutting elements 2012 and 2002 as one or both of the elements 2001, 2011 rotates, can allow for shearing of tissue. In the illustrated embodiment, outer component 2011 has a shaft (not shown) that fits into a bore 2010 formed in inner component 2001.

Figure 26A:
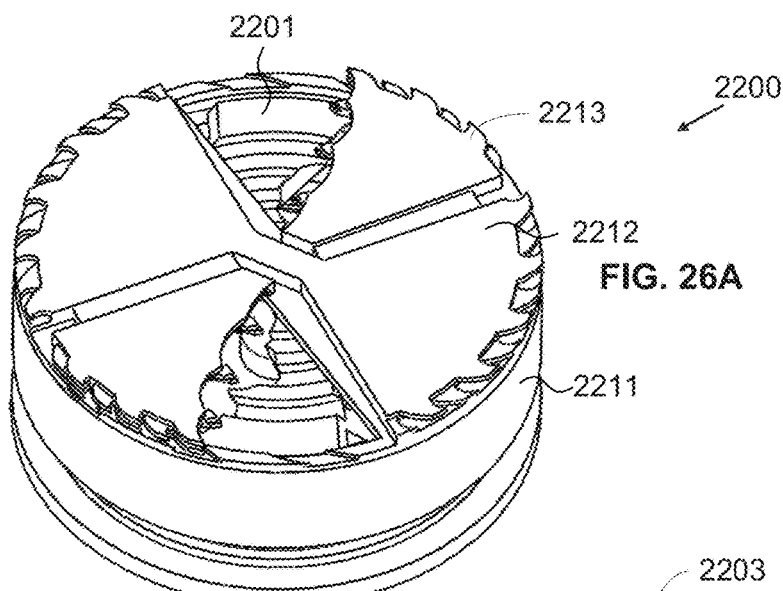
FIGS. 26A-26C illustrate an exemplary embodiment of a cutting device described herein.
Figure 26B:
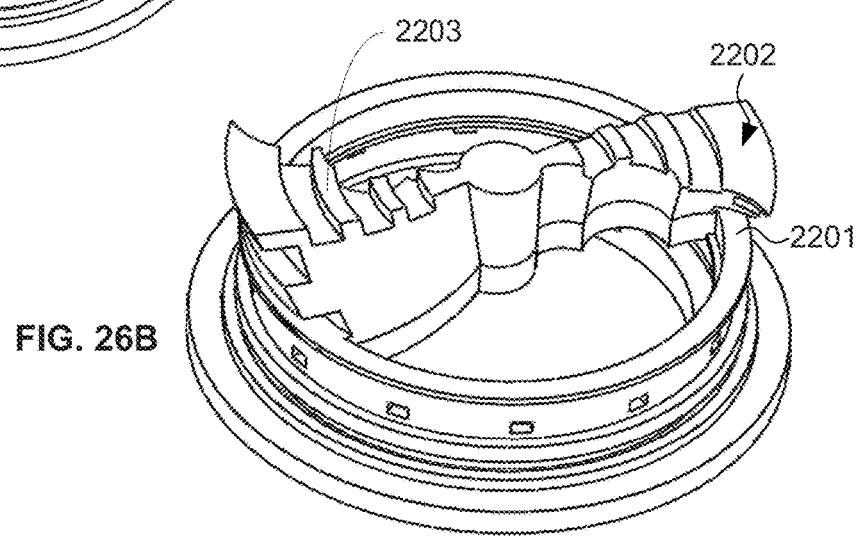
Figure 26C:
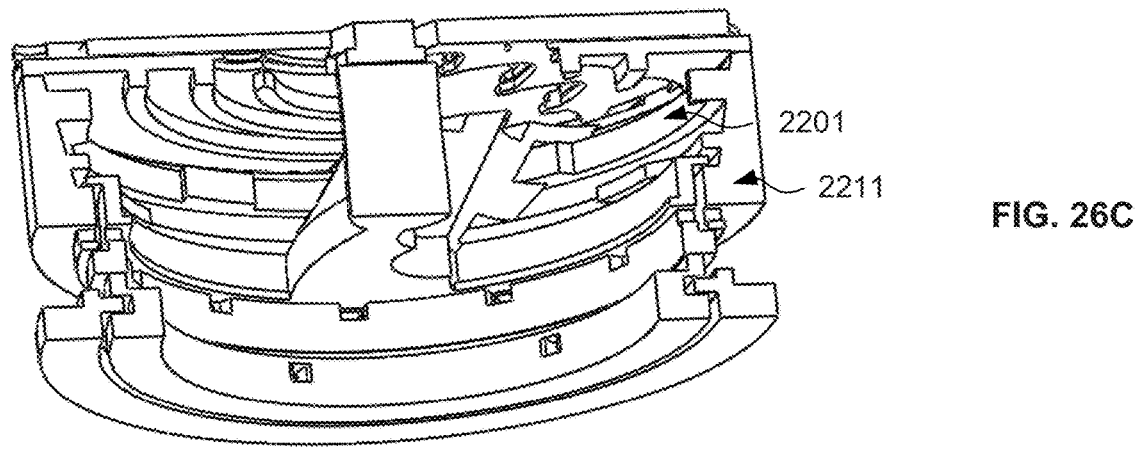

As shown in FIGS. 26A-26C, a cutting device 2200 can include an inner component 2201 and an outer component 2211. The inner component 2201 can include cutting surfaces 2202 having teeth 2203, while the outer component 2211 can include cutting surfaces 2212 having 2213. Inner component 2201 and outer component 2211 may be rotated with respect to each other so that cutting surfaces 2202 and 2212 can shear tissue extending through intake windows 2216. Other embodiments are possible. For example, the inner cutting element can include multiple cutters extending radially, while the outer cutting element includes multiple cutters extending axially. Alternatively, the inner cutting element can include multiple cutters extending axially while the outer cutter element also includes multiple cutters extending axially.

Figure 29:
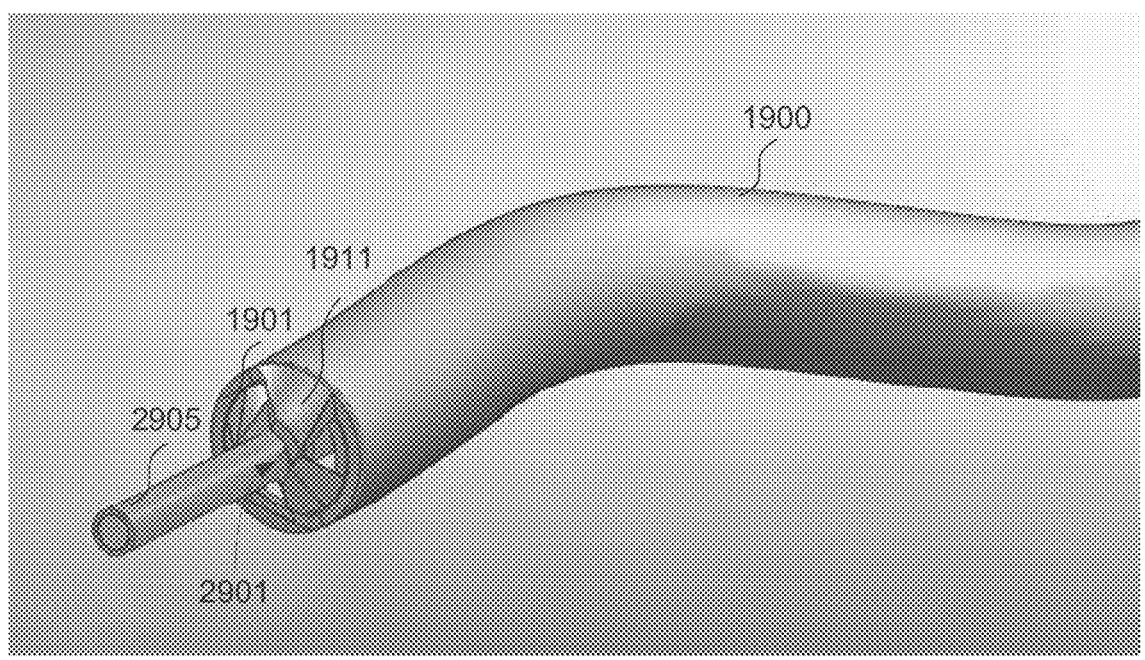
FIG. 29 illustrates an exemplary embodiment of a tissue cutting device having a working component extending therethrough.
Figure 30A:
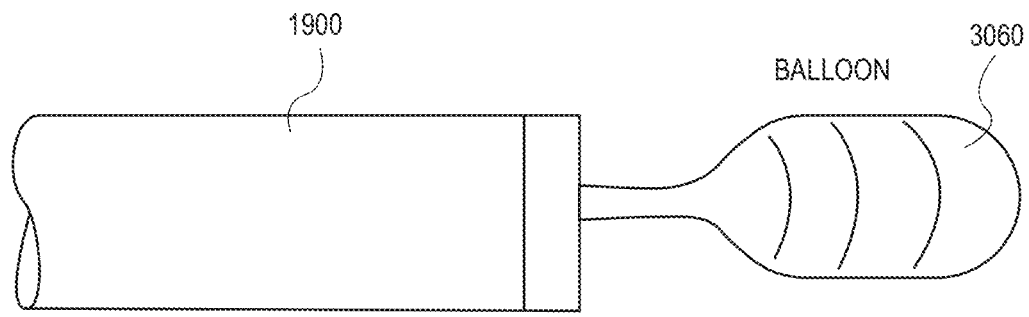
FIGS. 30A-30G illustrate exemplary embodiments of working components that can extend through the medical devices described herein.
Figure 30B:
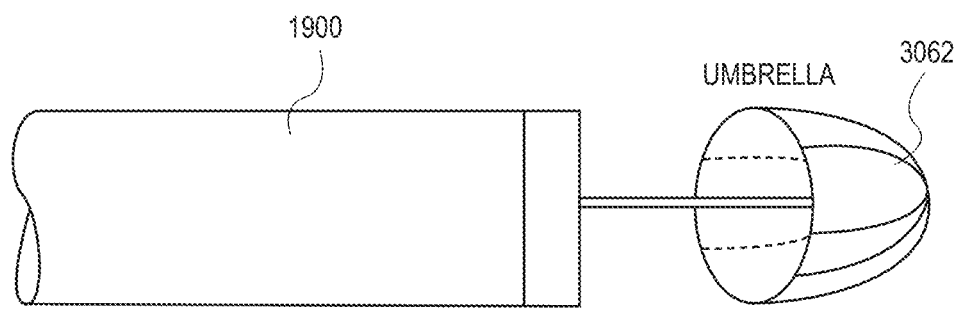
Figure 30C:
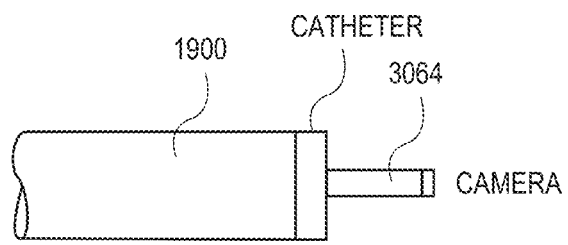
Figure 30D:
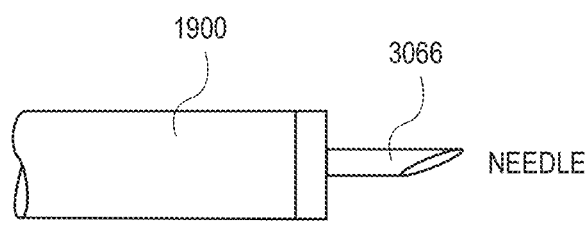
Figure 30E:
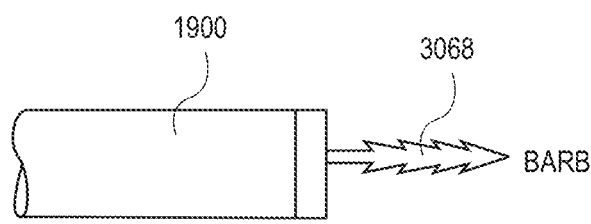
Figure 30F:
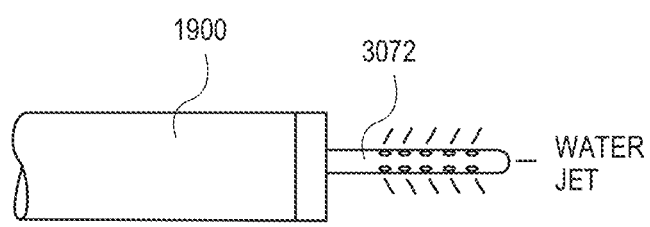
Figure 30G:
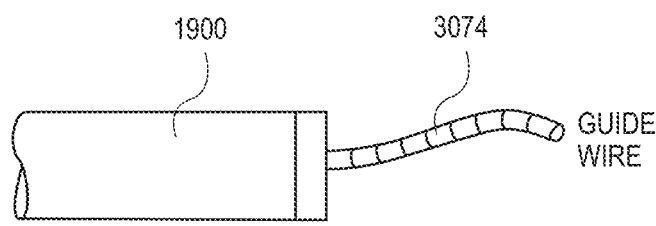

Further, referring to FIG. 29, the devices described herein, due to their small features sizes and precise build, can advantageously be configured to include ancillary components that extend along the inner central axis and through an opening in the distal end of the device. The cutting device 1900, representing any of the cutting devices described herein, can include including inner and outer cutting elements 1901 and 1911. A hole 2901 can extend along the central axis of the cutting device 1900. As such, an ancillary component 2905 can extend through the cutting device 1900. Referring to FIG. 30A, the ancillary component can be a balloon 3060. Referring to FIG. 30B, the ancillary component can be an umbrella 3062. Referring to FIG. 30C, the ancillary component can be an imaging element 3064, such as a CMOS camera, a fiber optic scope with CCD or CMOS, 2D and 3D capture and display, ultrasound (IVUS), Doppler, or birefringence-insensitive optical coherence tomography (OCT). Referring to FIG. 30D, the ancillary component can be a needle 3066, such as drug delivery needle. Referring to FIG. 30E, the ancillary component can be a longitudinal element 3068 including barbs to, for example, gather tissue and pull it towards the cutting elements or to stabilize tissue during cutting. Referring to FIG. 30F, the ancillary component can be a water jet tube 3072, such as a water jet tube for delivering water to clear clots. Referring to FIG. 30G, the ancillary component can be a guide wire 3074. Additional ancillary components include a device for suction, a device for irrigation, or an energy system to coagulate or cauterize, such as a system providing RF energy, an argon beam, a laser, or a DC current.

In summary, various specific cylindrical cutting device embodiments have been taught herein. These various device embodiments may make use of various elements including: (1) designs are driven with 2 concentric tubes; (2) cutting surfaces that face forward with respect to the longitudinal axis of the tool or instrument; (3) an inside tube is connected to one set of blades; (4) an outside tube is connected to one set of blades; (5) an inside tube is rotated with respect to the outside tubes, making the cutting blades pass one another; (6) in some cases the outside tube can be rotated in either direction at a different rate than the inside tube to expose all blades to the tissue at all azimuthal angles (this allows cutting over the entire front surface of the targeted area); (7) the various device embodiments can be attached to articulating tubes so that the cutting end can be steerable; (8) the various device embodiments can incorporate aspiration to remove the material that has been cut; (9) some embodiments may provide turbine or propeller-like effects which will help material transport away from the targeted area; (10) some embodiments may incorporate irrigation to aid in the material transport; (11) some embodiments may incorporate central imaging; (12) some embodiments may be deliverable via a central guide wire; (13) various embodiments are scalable to different radial sizes from less than one-half millimeter to more than a centimeter; and/or (14) some embodiments may be assisted by one or more proximally located supplement cutters, shredders, or mechanical flow assist devices.

Further Comments and Conclusions

Structural or sacrificial dielectric materials may be incorporated into embodiments of the present invention in a variety of different ways. Such materials may form a third material or higher deposited on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, filed Jan. 3, 2005 by Cohen, et al., now abandoned, and which is entitled "Electrochemical Fabrication Methods Incorporating Dielectric Materials and/or Using Dielectric Substrates". These patent filings are each hereby incorporated herein by reference as if set forth in full herein.

Some embodiments may employ diffusion bonding or the like to enhance adhesion between successive layers of material. Various teachings concerning the use of diffusion bonding in electrochemical fabrication processes are set forth in U.S. patent application Ser. No. 10/841,384 which was filed May 7, 2004 by Cohen et al., now abandoned, which is entitled "Method of Electrochemically Fabricating Multilayer Structures Having Improved Interlayer Adhesion" and which is hereby incorporated herein by reference as if set forth in full. This application is hereby incorporated herein by reference as if set forth in full.

Some embodiments may incorporate elements taught in conjunction with other medical devices as set forth in various U.S. patent applications filed by the owner of the present application and/or may benefit from combined use with these other medical devices: Some of these alternative devices have been described in the following previously filed patent applications: (1) U.S. patent application Ser. No. 11/478,934, by Cohen et al., and entitled "Electrochemical Fabrication Processes Incorporating Non-Platable Materials and/or Metals that are Difficult to Plate On"; (2) U.S. patent application Ser. No. 11/582,049, by Cohen, and entitled "Discrete or Continuous Tissue Capture Device and Method for Making"; (3) U.S. patent application Ser. No. 11/625,807, by Cohen, and entitled "Microdevices for Tissue Approximation and Retention, Methods for Using, and Methods for Making"; (4) U.S. patent application Ser. No. 11/696,722, by Cohen, and entitled "Biopsy Devices, Methods for Using, and Methods for Making"; (5) U.S. patent application Ser. No. 11/734,273, by Cohen, and entitled "Thrombectomy Devices and Methods for Making"; (6) U.S. Patent Application No. 60/942,200, by Cohen, and entitled "Micro-Umbrella Devices for Use in Medical Applications and Methods for Making Such Devices"; and (7) U.S. patent application Ser. No. 11/444,999, by Cohen, and entitled "Microtools and Methods for Fabricating Such Tools". Each of these applications is incorporated herein by reference as if set forth in full herein.

Though the embodiments explicitly set forth herein have considered multi-material layers to be formed one after another. In some embodiments, it is possible to form structures on a layer-by-layer basis but to deviate from a strict planar layer on planar layer build up process in favor of a process that interlaces material between the layers. Such alternative build processes are disclosed in U.S. application Ser. No. 10/434,519, filed on May 7, 2003, now U.S. Pat. No. 7,252,861, entitled Methods of and Apparatus for Electrochemically Fabricating Structures Via Interlaced Layers or Via Selective Etching and Filling of Voids. The techniques disclosed in this referenced application may be combined with the techniques and alternatives set forth explicitly herein to derive additional alternative embodiments. In particular, the structural features are still defined on a planar-layer-by-planar-layer basis but material associated with some layers are formed along with material for other layers such that interlacing of deposited material occurs. Such interlacing may lead to reduced structural distortion during formation or improved interlayer adhesion. This patent application is herein incorporated by reference as if set forth in full.

The patent applications and patents set forth below are hereby incorporated by reference herein as if set forth in full.

The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

Though various portions of this specification have been provided with headers, it is not intended that the headers be used to limit the application of teachings found in one portion of the specification from applying to other portions of the specification. For example, it should be understood that alternatives acknowledged in association with one

| U.S. patent application No., Filing Date U.S. application Pub No., Pub Date U.S. Pat. No., Pub Date | Inventor, Title |
|---|---|
| 09/493,496 - Jan. 28, 2000 U.S. Pat. No. 6,790,377 - Sep. 14, 2004 | Cohen, "Method For Electrochemical Fabrication" |
| 10/677,556 - Oct. 1, 2003 2004-0134772 - Jul. 15, 2004 | Cohen, "Monolithic Structures Including Alignment and/or Retention Fixtures for Accepting Components" |
| 10/830,262 - Apr. 21, 2004 2004-0251142A - Dec. 16, 2004 U.S. Pat. No. 7,198,704 - Apr. 3, 2007 | Cohen, "Methods of Reducing Interlayer Discontinuities in Electrochemically Fabricated Three-Dimensional Structures" |
| 10/271,574 - Oct. 15, 2002 2003-0127336A - Jul. 10, 2003 U.S. Pat. No. 7,288,178 - Oct. 30, 2007 | Cohen, "Methods of and Apparatus for Making High Aspect Ratio Microelectromechanical Structures" |
| 10/697,597 - Dec. 20, 2002 2004-0146650A - Jul. 29, 2004 | Lockard, "EFAB Methods and Apparatus Including Spray Metal or Powder Coating Processes" |
| 10/677,498 - Oct. 1, 2003 2004-0134788 - Jul. 15, 2004 U.S. Pat. No. 7,235,166 - Jun. 26, 2007 | Cohen, "Multi-cell Masks and Methods and Apparatus for Using Such Masks To Form Three-Dimensional Structures" |
| 10/724,513 - Nov. 26, 2003 2004-0147124 - Jul. 29, 2004 U.S. Pat. No. 7,368,044 - May 6, 2008 | Cohen, "Non-Conformable Masks and Methods and Apparatus for Forming Three-Dimensional Structures" |
| 10/607,931 - Jun. 27, 2003 2004-0140862 - Jul. 22, 2004 U.S. Pat. No. 7,239,219 - Jul. 3, 2007 | Brown, "Miniature RF and Microwave Components and Methods for Fabricating Such Components" |
| 10/841,100 - May 7, 2004 2005-0032362 - Feb. 10, 2005 U.S. Pat. No. 7,109,118 - Sep. 19, 2006 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-022168A - Dec. 4, 2003 | Cohen, "Electrochemical Fabrication Method and Application for Producing Three-Dimensional Structures Having Improved Surface Finish" |
| 10/434,494 - May 7, 2003 2004-0000489A - Jan. 1, 2004 | Zhang, "Methods and Apparatus for Monitoring Deposition Quality During Conformable Contact Mask Plating Operations" |
| 10/434,289 - May 7, 2003 20040065555A - Apr. 8, 2004 | Zhang, "Conformable Contact Masking Methods and Apparatus Utilizing In Situ Cathodic Activation of a Substrate" |
| 10/434,294 - May 7, 2003 2004-0065550A - Apr. 8, 2004 | Zhang, "Electrochemical Fabrication Methods With Enhanced Post Deposition Processing" |
| 10/434,295 - May 7, 2003 2004-0004001A - Jan. 8, 2004 | Cohen, "Method of and Apparatus for Forming Three-Dimensional Structures Integral With Semiconductor Based Circuitry" |
| 10/434,315 - May 7, 2003 2003-0234179 A - Dec. 25, 2003 U.S. Pat. No. 7,229,542 - Jun. 12, 2007 | Bang, "Methods of and Apparatus for Molding Structures Using Sacrificial Metal Patterns" |
| 10/434,103 - May 7, 2004 2004-0020782A - Feb. 5, 2004 U.S. Pat. No. 7,160,429 - Jan. 9, 2007 | Cohen, "Electrochemically Fabricated Hermetically Sealed Microstructures and Methods of and Apparatus for Producing Such Structures" |
| 10/841,006 - May 7, 2004 2005-0067292 - May 31, 2005 | Thompson, "Electrochemically Fabricated Structures Having Dielectric or Active Bases and Methods of and Apparatus for Producing Such Structures" |
| 10/434,519 - May 7, 2003 2004-0007470A - Jan. 15, 2004 U.S. Pat. No. 7,252,861 - Aug. 7, 2007 | Smalley, "Methods of and Apparatus for Electrochemically Fabricating Structures Via Interlaced Layers or Via Selective Etching and Filling of Voids" |
| 10/724,515 - Nov. 26, 2003 2004-0182716 - Sep. 23, 2004 U.S. Pat. No. 7,291,254 - Nov. 6, 2007 | Cohen, "Method for Electrochemically Forming Structures Including Non-Parallel Mating of Contact Masks and Substrates" |
| 10/841,347 - May 7, 2004 2005-0072681 - Apr. 7, 2005 | Cohen, "Multi-step Release Method for Electrochemically Fabricated Structures" |
| 60/533,947 - Dec. 31, 2003 | Kumar, "Probe Arrays and Method for Making" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |
| 11/733,195 - Apr. 9, 2007 2008-0050524 - Feb. 28, 2008 | Kumar, "Methods of Forming Three-Dimensional Structures Having Reduced Stress and/or Curvature" |
| 11/506,586 - Aug. 8, 2006 2007-0039828 - Feb. 22, 2007 | Cohen, "Mesoscale and Microscale Device Fabrication Methods Using Split Structures and Alignment Elements" |
| 10/949,744 - Sep. 24, 2004 2005-0126916 - Jun. 16, 2005 U.S. Pat. No. 7,498,714 - Mar. 3, 2009 | Lockard, "Three-Dimensional Structures Having Feature Sizes Smaller Than a Minimum Feature Size and Methods for Fabricating" | embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

What is claimed is:

1. A tissue cutting device comprising:
an elongate tube having a proximal end and a distal end and a central axis extending from the proximal end to the distal end, the tube being elongate in a direction along the central axis;
a first concentric element at the distal end of the elongate tube, the first concentric element having a flat portion at its distal end perpendicular to the central axis; and
a second concentric element at the distal end of the elongate tube and concentric with the first concentric element, the second concentric element having a flat portion at its distal end perpendicular to the central axis, at least one of the first or second concentric elements configured to rotate about the central axis relative to the other of the first and second concentric elements, the rotation causing the flat portion of the first concentric element and the flat portion of the second concentric element to pass each other to shear tissue against each other between the flat portions and to sever the tissue from a target tissue site,
wherein at least one of the flat portions is provided with cutting surfaces on opposite sides of the flat portion such that the cutting surfaces are axially spaced apart from one another, both of the opposite cutting surfaces being perpendicular to the central axis and configured to shear tissue against mating cutting surfaces located on the other of the first and second concentric elements, and
wherein the flat portion of at least one the first concentric element or the second concentric element extends to the central axis.

2. The tissue cutting device of claim 1 wherein the elongate tube has a diameter less than 5 mm.

3. The tissue cutting device of claim 1 wherein at least one of the first and second concentric elements has a tooth having a radial thickness of less than 50 microns.

4. The tissue cutting device of claim 1, wherein the flat portion of the first concentric element has an axial thickness of less than 100 microns.

5. The tissue cutting device of claim 1 wherein the first concentric element comprises a pair of inner pinch-off cutters spaced apart circumferentially, and wherein the second concentric element comprises at least one outer pinch-off cutter, the inner and the outer pinch-off cutters being configured to pass each other to shear tissue therebetween when at least one of the first or second concentric elements is rotated about the central axis.

6. The tissue cutting device of claim 5 wherein the inner and the outer pinch-off cutters further comprise interlaced side cutters configured for side milling, the side cutters each comprising cutting surfaces that are parallel to the central axis, a cutting surface of a side cutter associated with an inner pinch-off cutter configured to cooperate with a cutting surface of a side cutter associated with an outer pinch-off cutter to shear tissue therebetween.

7. The tissue cutting device of claim 6, wherein the cutting surfaces of two of the side cutters are each associated with one of the circumferentially spaced apart inner pinch-off cutters and extend along a common radial plane.

8. The tissue cutting device of claim 6, wherein each of the pair of inner pinch-off cutters has a plurality of side cutters associated with it, approximately axially aligned thereto, and spaced apart axially from the outer pinch-off cutter.

9. The tissue cutting device of claim 8, wherein each of the pair of inner pinch-off cutters has exactly three side cutters associated with it.

10. The tissue cutting device of claim 6, wherein at least one of the side cutters further comprises a cutting surface extending perpendicular to the central axis and configured to cooperate with a cutting surface of an opposing side cutter to shear tissue therebetween.

11. The tissue cutting device of claim 1, wherein the first and second concentric elements comprise interlaced side cutters that provide for side milling, the side cutters being spaced apart axially.

12. The tissue cutting device of claim 1, wherein at least one of the first or second concentric elements is configured to be driven by a prime mover to continuously rotate about the central axis relative to the other of the first and second concentric elements.

13. A tissue cutting device, comprising:
an elongate tube having a proximal end and a distal end and a central axis extending from the proximal end to the distal end, the tube being elongate in a direction along the central axis;
a first concentric element at the distal end of the elongate tube, the first concentric element including a plurality of first shearing elements, each first shearing element having a perpendicular shearing surface that is perpendicular to the central axis;
a second concentric element at the distal end of the elongate tube and concentric with the first concentric element, the second concentric element including a plurality of second shearing elements, each second shearing element having a perpendicular shearing surface that is perpendicular to the central axis,
wherein at least one of the first or second concentric elements is configured to rotate about the central axis, the rotation causing the perpendicular shearing surfaces of the first shearing elements and the perpendicular shearing surfaces of the second shearing elements to pass each other to shear tissue against each other and to sever the tissue from a target tissue site,
wherein at least one of the first and second shearing elements is provided with at least two of the shearing surfaces located on opposite sides of the shearing element such that the shearing surfaces are axially spaced apart from one another, both of the opposite shearing surfaces being perpendicular to the central axis and configured to shear tissue against mating shearing surfaces located on the other of the first and second shearing elements, and
wherein the first concentric element or the second concentric element extends to the central axis.

14. The tissue cutting device of claim 13, wherein at least some of the perpendicular shearing surfaces of the first shearing elements lie along the same plane.

15. The tissue cutting device of claim 12, wherein the at least some of the perpendicular shearing surfaces of the first shearing elements are located at the same radial distance from the central axis.

16. The tissue cutting device of claim 13, wherein the at least some perpendicular shearing surfaces are located at different radial distances from the central axis.

17. The tissue cutting device of claim 13, wherein each first shearing element has a parallel shearing surface that is parallel to the central axis;
   wherein each second shearing element has a parallel shearing surface that is parallel to the central axis;
   wherein the parallel shearing surfaces of the first shearing elements and the parallel shearing surfaces of the second shearing elements can interlace with one another in an axial direction; and
   wherein rotation of one or both of the first and second concentric elements causes the parallel shearing surfaces of the first shearing elements and the parallel shearing surfaces of the second shearing elements to pass each other to shear tissue therebetween.

18. The tissue cutting device of claim 17, wherein at least some of the parallel shearing surfaces of the first shearing elements lie along the same radial plane.

19. The tissue cutting device of claim 18, wherein the at least some parallel shearing surfaces of the first shearing elements are spaced apart from each other circumferentially.

20. The tissue cutting device of claim 17, wherein at least some of the parallel shearing surfaces of the first shearing elements are spaced apart from each other radially.

21. The tissue cutting device of claim 13, wherein the elongate tube has a diameter of less than 5 mm.

\* \* \* \* \*